United States Patent
Windsor et al.

(10) Patent No.: US 6,645,966 B2
(45) Date of Patent: Nov. 11, 2003

(54) TREATMENT OF MALARIA WITH FARNESYL PROTEIN TRANSFERASE INHIBITORS

(75) Inventors: William T. Windsor, East Brunswick, NJ (US); Patricia C. Weber, Yardley, PA (US); Corey O. Strickland, Martinsville, NJ (US); Michael Gelb, Seattle, WA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/053,335

(22) Filed: Jan. 18, 2002

(65) Prior Publication Data

US 2003/0092705 A1 May 15, 2003

Related U.S. Application Data

(60) Provisional application No. 60/263,277, filed on Jan. 22, 2001.

(51) Int. Cl.[7] .................. A61K 31/495; A61K 31/47
(52) U.S. Cl. ................ 514/253.03; 514/311; 514/895
(58) Field of Search ............ 514/253.03, 311, 514/895

(56) References Cited

U.S. PATENT DOCUMENTS

| | | | |
|---|---|---|---|
| 5,089,496 A | 2/1992 | Piwinski et al. | 514/253.03 |
| 5,874,442 A | 2/1999 | Doll et al. | 514/290 |
| 5,965,570 A * | 10/1999 | Cooper et al. | 514/290 |
| 6,011,029 A | 1/2000 | Ding et al. | 514/221 |
| 6,037,350 A | 3/2000 | Venet et al. | 514/312 |
| 6,071,907 A * | 6/2000 | Njoroge et al. | 514/228.2 |
| 6,387,905 B2 * | 5/2002 | Njoroge et al. | 514/253.03 |

FOREIGN PATENT DOCUMENTS

| | | |
|---|---|---|
| WO | WO 97/30992 | 8/1997 |
| WO | WO 98/11098 | 3/1998 |
| WO | WO 98/57960 | 12/1998 |
| WO | WO 00/37458 | 6/2000 |
| WO | WO 00/37459 | 6/2000 |

OTHER PUBLICATIONS

*Molecular and Biochemical Parasitology*, vol 94, No. 2, (1998) pp 175–184.
*Tetrahedron Letters*, vol. 31, No. 39, (1990) pp 5595–5598.
*Science*, vol. 285 (1999) pp 1573–1576.
Emmett, J.C. et al., *J. Chem. Soc.*, Perkin Trans. 1 (1979) pp 1341–1344.

* cited by examiner

Primary Examiner—Kevin E. Weddington
(74) Attorney, Agent, or Firm—Robert L. Bernstein

(57) ABSTRACT

Disclosed is a method of treating Malaria comprising administering an effective amount of an FPT inhibitor to a patient in need of such treatment alone or in combination with an additional antimalarial agent and/or agent for reversing antimalarial resistance.

Also disclosed are novel Farnesyl Protein Transferase inhibitors.

9 Claims, No Drawings

TREATMENT OF MALARIA WITH FARNESYL PROTEIN TRANSFERASE INHIBITORS

REFERENCE TO RELATED APPLICATIONS

This application claims the benefit of U.S. Provisional Application Serial No. 60/263,277 filed Jan. 22, 2001.

FIELD OF THE INVENTION

The present invention relates to a method of treating malaria comprising administering an effective amount of an FPT inhibitor to a patient in need of such treatment alone or in combination with an additional antimalarial agent and/or agent for reversing antimalarial resistance.

The present invention also relates to novel Farnesyl Protein Transferase inhibitors, methods of preparing such inhibitors, compositions containing such inhibitors and methods of using such inhibitors in the treatment of malaria.

BACKGROUND

Malaria is one of the most widespread infectious diseases in the world infecting over 200 million people of which, it has been estimated, 1–2 million die from the disease per year.

Malaria is a disease caused by a parasite transmitted by the bite of an infected female Anopheles mosquito. When an infecting sporozoite parasite enters the bloodstream it rapidly infects both liver and red blood cells and differentiates into merozoites. Asexual reproduction of the merozoite within erythrocytes results in the rupture and subsequent reinfection of other red blood cells. This cyclic process results in clinical symptoms of headaches, sweating, vomiting, malaise, delirium and acute fever and may be fatal if not treated.

There are four main species, which infect humans, *Plasmodium vivax, Plasmodium malariae, Plasmodium ovale,* and *Plasmodium faliciparum.* Several anitmalarial drugs have been developed to treat the disease. Chloroquine and quinine have been used widely for over forty years because they have been exceptionally safe, inexpensive and effective drugs for treating the disease. Recently, however, chloroquine- and quinine-resistant strains of *P. faliciparum* have developed and are causing high levels of mortality. In an effort to identify a new and more effective method for treating malaria, Chakrabarti et. al., have studied the use of inhibitors of prenyl transferases from the malaria parasite, *Plasmodium falciparum*, in an effort to identify a method for treating malaria, see Chakrabarti, et al., Molecular and Biochemical Parasitology (1998) 94, 175–184.

In view of the need to find new treatments of malaria, those skilled in the art would welcome an effective method for the treatment of malaria. The present invention provides such a method utilizing inhibitors of *Plasmodium falciparum* protein prenyl transferases.

SUMMARY OF THE INVENTION

This invention provides a method of treating and/or preventing malaria comprising administering to a patient, in need of such treatment, an effective amount (e.g., a therapeutically effective amount, or an amount to inhibit malaria) of a Farnesyl Protein Transferase inhibitor selected from Compounds 1–26 described below.

This invention also provides novel compounds (i.e., novel FPT inhibitors) selected from the compounds: 14, or 16–23 described below.

DETAILED DESCRIPTION

As used herein, the following terms are used as defined below unless otherwise indicated:

$MH^+$-represents the molecular ion plus hydrogen of the molecule in the mass spectrum;

BOC-represents-t-BOC-represents-tert-butyloxycarbonyl;

CBZ-represents $—C(O)OCH_2C_6H_5$ (i.e., benzyloxycarbonyl);

$CH_3CN$-represents-acetonitrile;

$CDCl_3$-represents-deuterated chloroform $CH_2Cl_2$-represents dichloromethane;

CIMS-represents chemical ionization mass spectroscopy;

DEA-represents diethyl amine;

DMSO-represents dimethyl sulfoxide

DMF-represents N,N-dimethylformamide;

EI-represents electron ionization spectroscopy;

Et-represents ethyl;

$Et_2O$-represents diethyl ether;

EtOAc-represents ethyl acetate;

EtOH-represents ethanol;

HCl-represents hydrochloric acid

IPA-represents isopropanol;

LAH-represents lithium aluminum hydride;

LCMS-represents liquid chromatography mass spectroscopy;

Me-represents methyl;

MeOH-represents methanol;

$MgSO_4$-represents magnesium sulfate;

MS-represents mass spectroscopy;

FAB-represents FABMS which represents fast atom bombardment mass spectroscopy;

HRMS-represents high resolution mass spectroscopy;

NaOH-represents sodium hydroxide;

$Na_2SO_4$-represents sodium sulfate;

$NaHCO_3$-represents sodium bicarbonate;

$NH_4OH$-represents amonium hydroxide;

NOE-represents nuclear Overhauser effect;

NMR-represents nuclear magnetic resonance spectroscopy;

NMM-represents N-methylmorpholine;

p-TosCl-represents p-toluenesulfonyl chloride;

$P_2O_5$-represents phosphorous pentoxide;

Pr-represents propyl;

$Et_3N$-represents TEA which represents triethylamine;

t-BUTYL-represents $—C—(CH_3)_3$;

TFA-represents trifluoroacetic acid;

THF-represents tetrahydrofuran;

TLC-represents thin layer chromatography;

FPT-represents Farnesyl Protein Transferase

One skilled in the art will appreciate that the positions of the Nitrogen atoms around the imidazole portion of the compounds described below are:

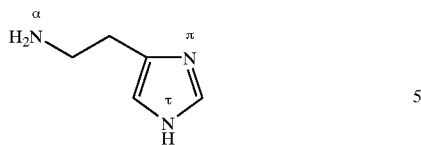
5
The FPT inhibitors useful in the claimed invention are:
| Cmpd. # | STRUCTURE |
|---|---|
| 1 | 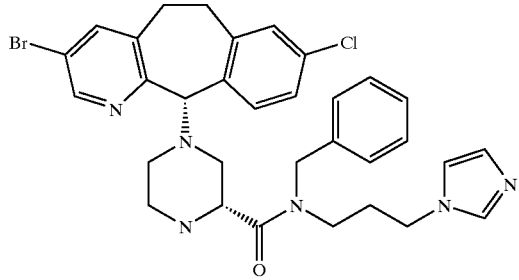<br>see WO 00/37459 |
| 2 | 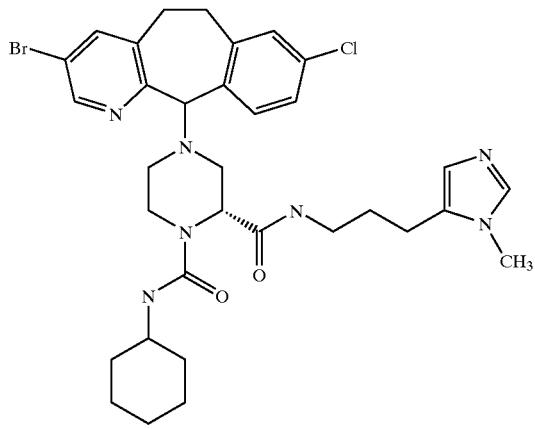<br>see WO 00/37459 |
| 3 | 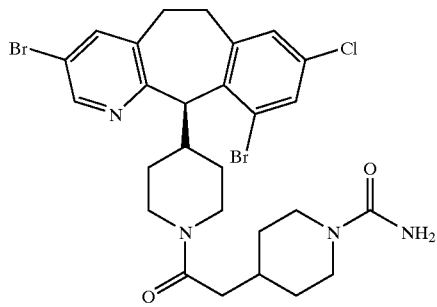<br>see U.S. Pat. No. 5,874,442 |

-continued
| Cmpd. # | STRUCTURE |
|---|---|
| 4 | 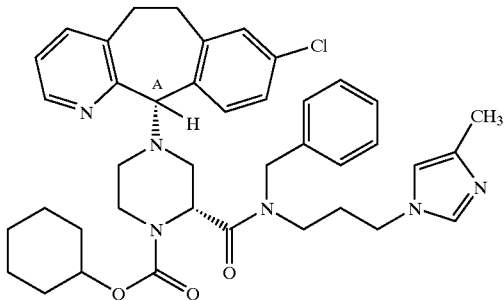<br>see WO 00/37459 |
| 5 | 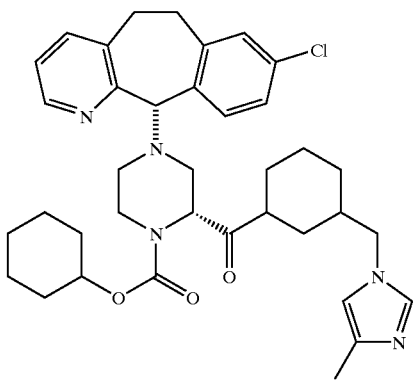<br>see WO 00/37458 |
| 6 | 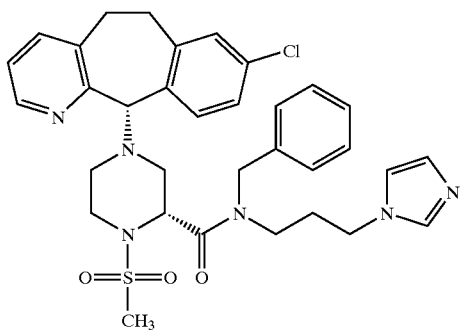<br>see WO 00/37459 |
| 7 | 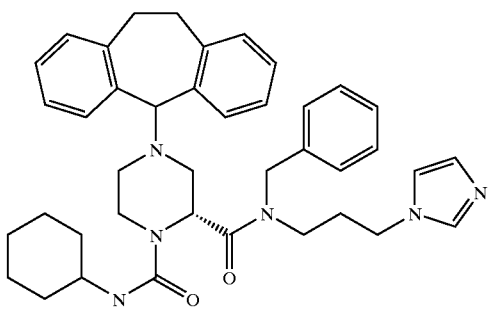<br>see WO 00/37459 |

-continued
| Cmpd. # | STRUCTURE |
|---|---|
| 8 | 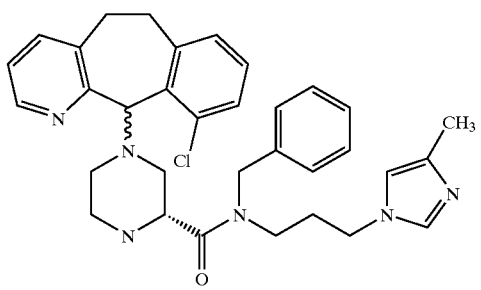<br>see WO 00/37459 |
| 9 | 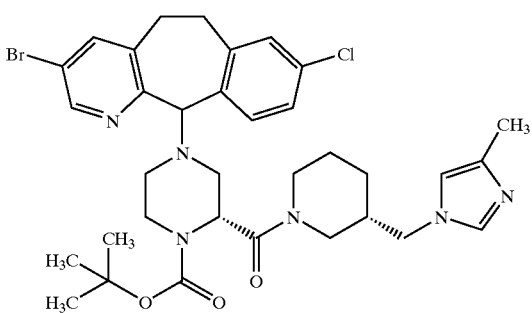<br>see WO 00/37458 |
| 10 | 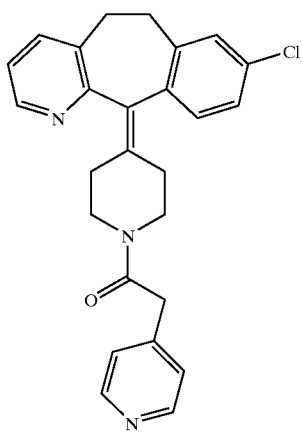<br>see U.S. Pat. No. 5,089,496 |
| 11 | 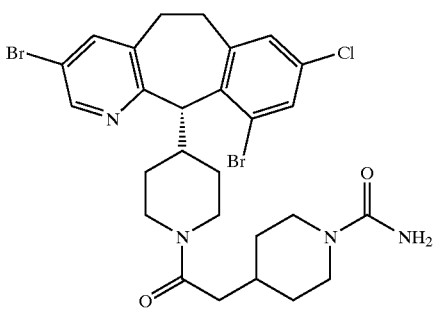<br>see U.S. Pat. No. 5,874,442 |

-continued
| Cmpd. # | STRUCTURE |
|---|---|
| 12 | 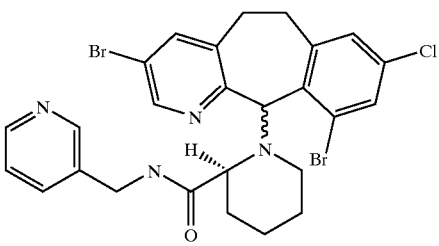<br>see WO 98/11098 |
| 13 | 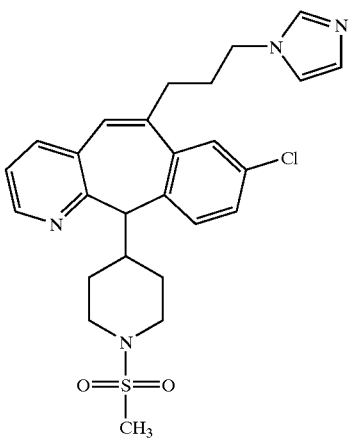<br>see Example 9, below |
| 14 | 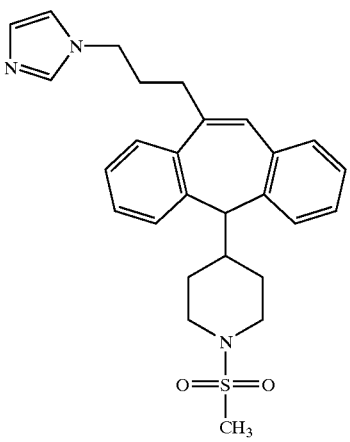<br>see Example 10, below |

-continued

| Cmpd. # | STRUCTURE |
|---|---|
| 15 | see WO 98/57960 |
| 16 | see Example 5, below |
| 17 | see Example 6, below |
| 18 | see Example 7, below |

-continued
| Cmpd. # | STRUCTURE |
|---|---|
| 19 | 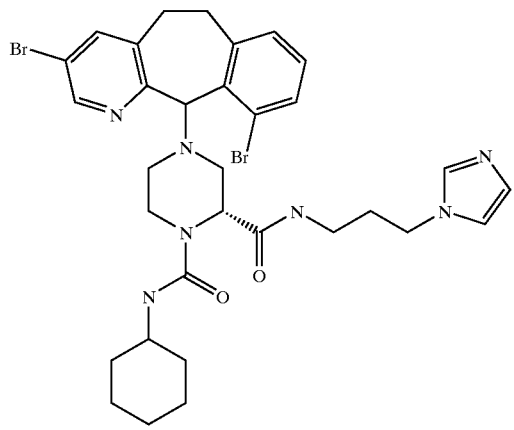<br>see Example 8, below |
| 20 | 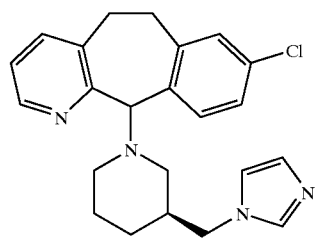<br>see Example 3, below |
| 21 | 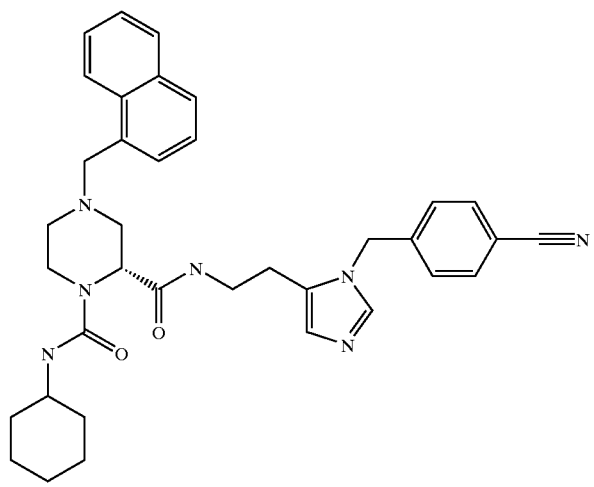<br>see Example 1, below |

-continued
| Cmpd. # | STRUCTURE |
|---|---|
| 22 | 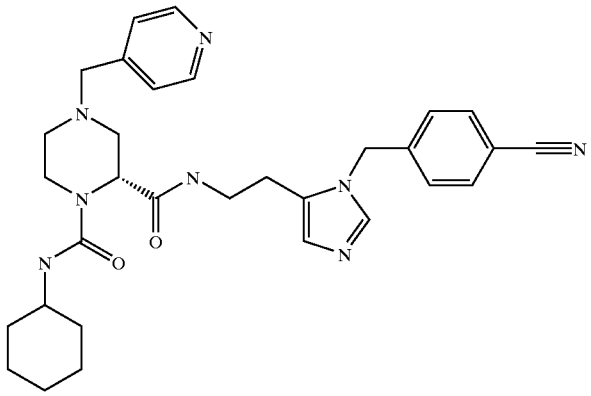<br>see Example 2, below |
| 23 | 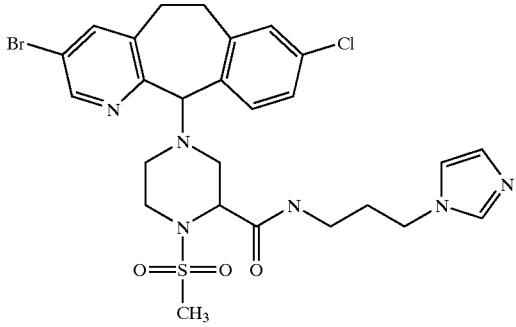<br>see Example 4, below |
| 24 | 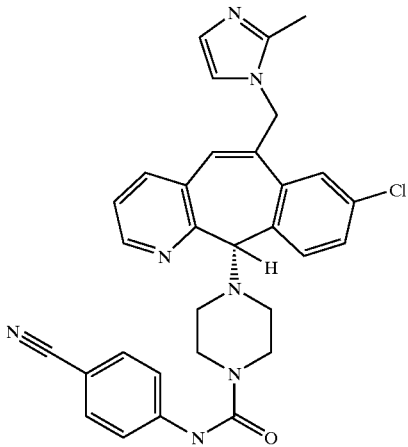<br>see Example 11 below |

-continued
| Cmpd. # | STRUCTURE |
|---|---|
| 25 | 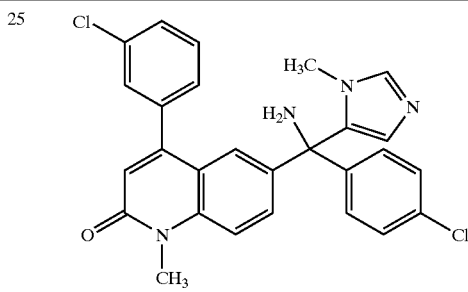<br>see WO 97/16443 |
| 26 | 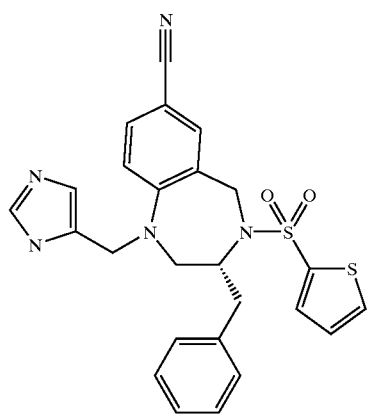<br>see WO 97/30992 |
Preferably the compound (3)
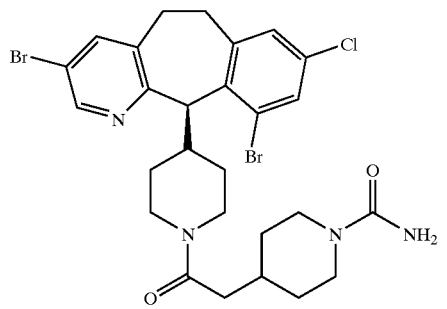
is used in the methods of this application.

The novel FPT inhibitory compounds are:
| Cmpd. # | STRUCTURE |
|---|---|
| 14 | 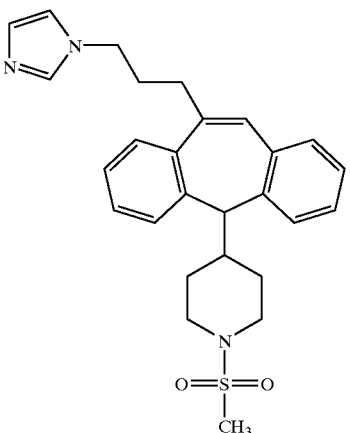 |
| 16 | 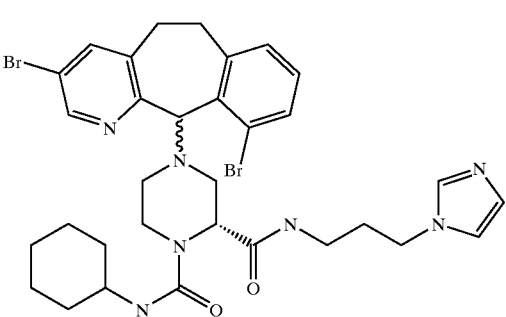 |
| 17 | 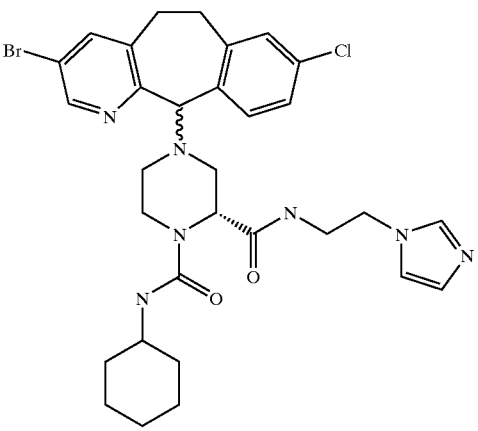 |
| 18 | 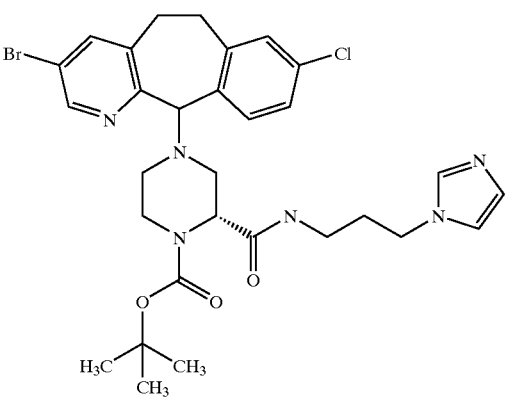 |

| Cmpd. # | STRUCTURE |
|---|---|
| 19 | 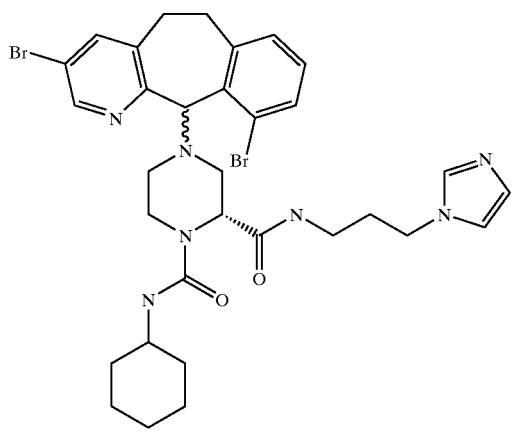 |
| 20 | 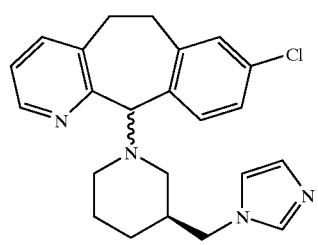 |
| 21 | 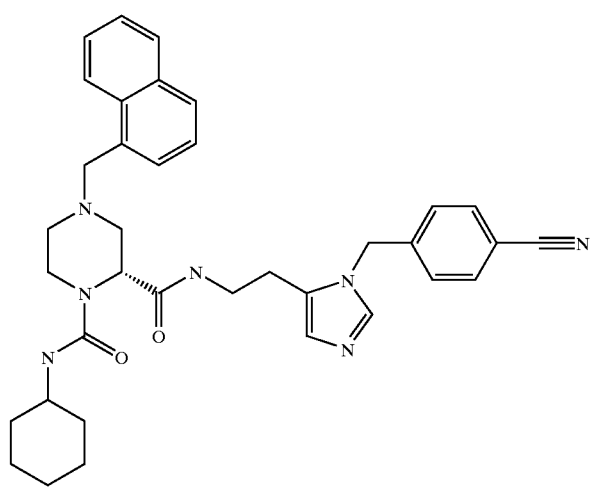 |
| 22 | 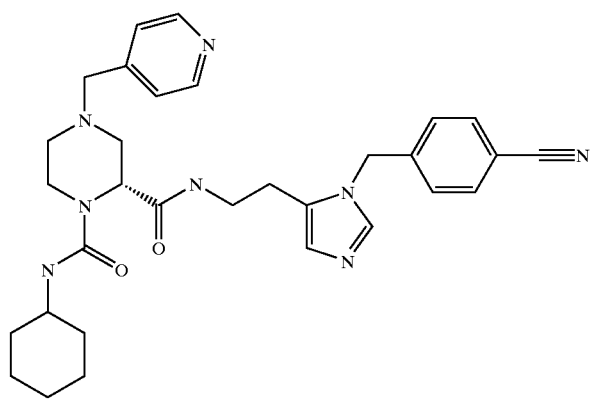 |

| Cmpd. # | STRUCTURE |
|---|---|
| 23 | 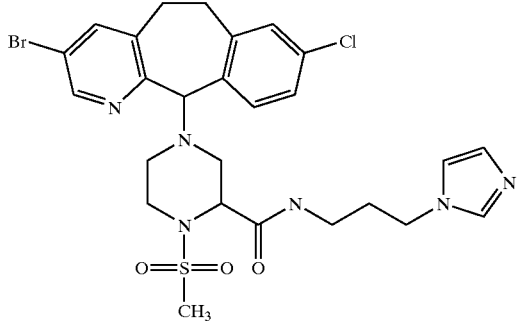 |

In another embodiment, this invention provides a method of treating malaria, wherein, the compounds 1–26 described herein above, are administered in combination with an additional antimalarial agent and/or an antimalarial resistance reversing agent. In general, additional antimalarial agents and/or antimalarial resistance reversing agents are ones known in the art to treat or prevent malaria, such as, for example quinolines (e.g. Chloroquine), folic acid antagonists (e.g. pyrimethamine), sulfonamides (e.g. sulfadiazine), antibiotics (e.g. tetracycline) and/or inhibitors of multidrug resistance (e.g. tetrandrine).

In general, in combination with, means, the additional antimalarial agents and/or antimalarial resistance reversing agents may be administered prior to, concurrent with, or subsequent to, the administration of a therapeutically effective amount of a compound selected from 1–26.

Compounds useful in this invention are exemplified by the following examples, which should not be construed to limit the scope of the disclosure.

EXAMPLES

Preparative Example 1

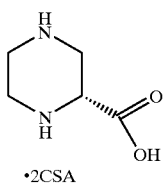

30

•2CSA

To 2.5 kg of (R)-(-)-camphorsulfonic acid stirring at 60° C. in 1250 ml of distilled water was added a solution of the potassium salt of 2-carboxyl-piperazine (565 gm, 3.35 mol). The mixture was allowed to stir at 95° C. until completely dissolved. The solution was allowed to stand at ambient temperature for 48 hrs. The resulting precipitate was filtered to obtain 1444 gm of damp solid. The solids were then dissolved in 1200 ml of distilled water and heated on a steam bath until all solids dissolved. The hot solution was then set aside to cool slowly for 72 hrs. The crystalline solids were filtered to give 362 gm of pure product (30) as a white crystalline solid. $[\alpha]_D = -14.9°$ Preparative Example 2

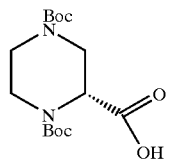

31

2-R-carboxyl-piperazine-di-(R)-(-)-camphorsulfonic (362 gm, 0.608 mol) was dissolved in 1.4 L of distilled water and 1.4 L of methanol. 75 ml of 50% NaOH was dripped into the stirred reaction mixture to obtain a ~pH 9.5 solution. To this solution was added di-tert.butyl-dicarbonate (336 gm, 1.54 mol) as a solid. The pH dropped to ~7.0. The pH of the reaction mixture was maintained at 9.5 with 50% NaOH (total of 175 ml), and the reaction mixture stirred for 2.5 hours to obtain a white precipitate. The reaction mixture was diluted to 9 L with ice/water followed by washing with 2 L of ether. The ether was discarded and the pH of the aqueous layer adjusted to pH 3.0 by the portion wise addition of solid citric acid. The acidified aqueous layer was then extracted with dichloromethane 3× with 2 L. The organic layers were combined, dried over sodium sulfate, filtered and evaporated to obtain 201.6 gm of title compound (31) as a white glassy solid. FABMS (M+1)=331

Preparative Example 3

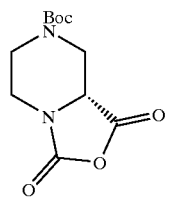

32

To an ice cold solution N,N-dimethylformamide (49.6 ml) was added, drop wise, thionylchloride (46.7 ml) over a period of 5 minutes in a 5 L round bottom flask under a nitrogen atmosphere. The reaction mixture was allowed to stir for 5 min. and the ice bath removed and the reaction mixture allowed to stir at ambient temperature for 30 min. The reaction mixture was cooled again in an ice bath and a solution of N,N-di-butoxycarbonyl-2-R-carboxyl-piperazine (201.6 gm, 0.61 mmol) in 51.7 ml of pyridine and 1.9 L of acetonitrile was cannulated into the reaction mixture. The reaction mixture was allowed to warm to ambient to obtain a yellowish turbid solution. After stirring at ambient temperature for 18 hours, the reaction mixture was filtered and the filtrate poured into ice water (7 L) and then extracted with 4×2 L of ethylacetate, dried over sodium sulfate, filtered and evaporated to dryness under vacuo to obtain 115.6 gm (73%) of the title product (32) as a white solid.

Preparative Example 4

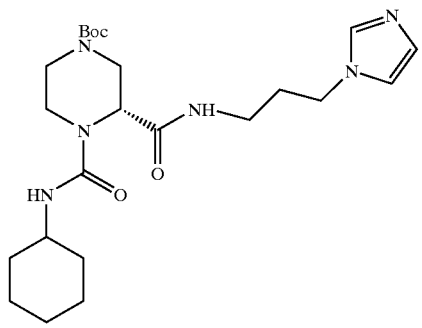

33

Compound (32) from Preparative Example 3 (0.84 gm, 3.3 mmol) was dissolved in 15 ml of dichloromethane. 1-(3-aminopropyl)imidazole) (0.4 ml, 3.3 mmol) was added drop wise and the reaction stirred at room temperature for 2 hours. After 2 hours 0.2 ml more of 1-(3-aminopropyl) imidazole) was added and the reaction mixture stirred for 2 hours. Cyclohexylisocyanide (0.86 ml, 6.7 mmol) was added drop wise and the reaction mixture stirred for 4 hours. After washing with brine, the dichloromethane was concentrated to dryness and the residue chromatographed on silica gel to obtain the title product (33) (0.9 gm) which was utilized in the next step.

Preparative Example 5

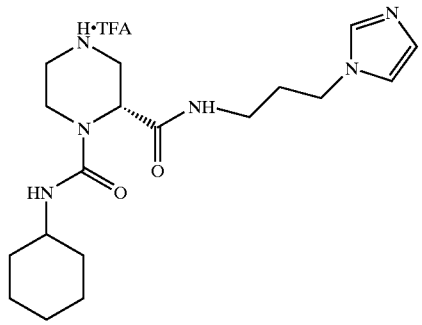

34

Compound (33) from Preparative Example 4 above, was treated with trifluoroacetic acid for 1 hour. The reaction mixture was evaporated to dryness and was then evaporated from toluene 3 times to obtain the product (34) as an oil (0.9 gm).

Preparative Example 6

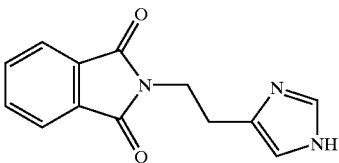

35

N-Carbethoxyphthalimide (62.8 g, 0.275 mol, 1.1 eq.) was added portion wise over a period of 30 minutes to a stirred solution of histamine dihydrochloride (46.7 g, 0.250 mol, 1.0 eq.) and sodium carbonate (54.3 g, 0.513 mol, 2.05 eq.) in distilled water (1250 ml) at room temperature. The resulting snow-white suspension was stirred vigorously at room temperature for 90 minutes. The solid was filtered off and thoroughly washed with ice-cold distilled water (4×50 ml). The solid was collected and dried under vacuum over $P_2O_5$ at 60° C. for 12 h to give $N^\alpha$-phthaloylhistamine(35) (59.2 g, 0.245 mol, 98%) in high purity (>95% by $^1$H NMR). The snow-white solid (35) was used directly without further purification.

$^1$H NMR (CDCl$_3$, 200 MHz): δ9.50–9.25 (br. s, 1H), 7.80–7.60 (m, 5H), 6.90 (s, 1H), 3.98 (t, 2H, J=7.0 Hz), 3.06 (t, 2H, J=7.0 Hz). MS (EI): m/e 241 (M$^+$, 15%), 160 (34), 94 (B$^+$).

mp 189–191° C. (ethanol, 190 proof).

Reference: Emmett, J. C., Holloway, F. H., Turner, J. L. J. Chem. Soc., Perkin Trans. 1 1979,1341–1344.

Preparative Example 7

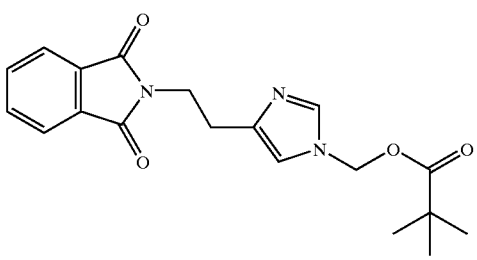

36

A solution of chloromethyl pivalate (18.5 ml, 0.125 mol, 1.2 eq.) in anhydrous N,N-dimethylformamide (DMF, 100 ml) was added drop wise over a period of one hour to a stirred mixture of Compound (35) (25.0 g, 0.104 mol, 1.0 eq.) and potassium carbonate (17.2 g, 0.125 mol, 1.2 eq.) in anhydrous DMF (500 ml) at 90° C. under a nitrogen atmosphere. The mixture was stirred at 90° C. for 12 h. The volatiles were removed under vacuum at 50° C. The residue was taken up in brine (100 ml) and extracted with ethyl acetate (4×25 ml). The combined organic extracts were dried over Na$_2$SO$_4$, filtered, and concentrated under vacuum at 30° C. The residual off-white solid was flash-chromatographed (hexanes: acetone=6:4 v/v) over silica gel to give $N^\tau$-pivaloyloxymethyl-$N^\alpha$-phthaloylhistamine 4 (20 g, 0.056 mol, 54%) as a crystalline, white solid (36) of high purity (>95% by $^1$H NMR).

$^1$H NMR (CDCl$_3$, 200 MHz): δ7.87–7.76 (m, 2H), 7.75–7.65 (m, 3H), 6.89 (s, 1H), 5.78 (s, 2H), 4.00 (t, 2H, J=7.1 Hz), 2.99 (t, 2H, J=7.1 Hz), 1.14 (s, 9H).

(NOE experiments unequivocally confirmed that the $N^\tau$ isomer was exclusively isolated.)

MS (FAB+): m/e 356 ([M+H]+).

HR-MS (FAB):Calculated for $C_{19}H_{22}N_3O_4$ ([M+H]+): 356.1610. Found: 356.1613.

mp: 126–128° C.

Preparative Example 8

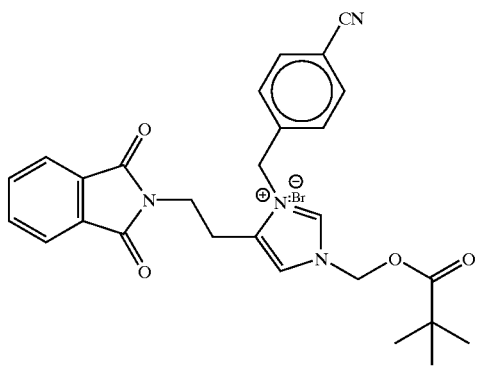

A solution of Compound (36) (10.2 g, 28.7 mmol, 1.0 eq.) and α-bromo-p-tolunitrile (11.4 g, 57.4 mmol, 2.0 eq.) was stirred in anhydrous acetonitrile (150 ml) at 50° C. under a nitrogen atmosphere for 12 h. The resulting snow-white suspension was cooled to room temperature and chilled in a refrigerator at −20° C. for one hour. The precipitate was filtered off and thoroughly washed with ice-cold ethyl acetate (4×50 ml). The solid was collected and dried under vacuum over $P_2O_5$ at 50° C. for 12 h to give Compound (37) (14.4 g, 26.2 mmol) in 91% yield. The hygroscopic salt (37) was more than 95% pure by $^1$H NMR and was used directly without any attempts at purification.

$^1$H NMR (CD$_3$OD, 200 MHz): δ7.80–7.70 (m, 8H), 7.57–7.45 (m, 2H), 6.09 (s, 2H), 5.66 (s, 2H), 3.90 (t, 2H, J=6.4 Hz), 3.05 (t, 2H, J=6.4 Hz), 1.17 (s, 9H).

Preparative Example 9

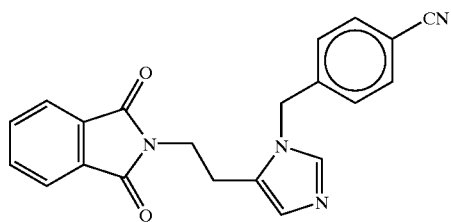

A 7 N solution of ammonia in methanol (75 ml, 0.525 mol, 7.25 eq.) was added drop wise over a period of 75 minutes to a stirred solution of Compound (37) (40 g, 0.073 mol, 1.00 eq.) in anhydrous methanol (1000 ml) at 0° C. under a nitrogen atmosphere. The mixture was slowly (3 h) warmed to ambient temperature and stirred for another 12 h. The volatiles were evaporated under vacuum at 30° C. and the residual white solid was flash-chromatographed (CH$_2$Cl$_2$:2 N NH$_3$/MeOH=90:10 v/v) over silica gel to give N$^\pi$-(4-cyanobenzyl)-N$^\alpha$-phthaloylhistamine Compound (38) (21 g, 0.059 mol, 81%).

$^1$H NMR (CDCl$_3$, 200 MHz): δ7.87–7.70 (m, 4H), 7.68 (s, 1H), 7.63 (d, 2H, J=8.4 Hz), 7.20 (d, 2H, J=8.4 Hz), 6.98 (s, 1H), 5.31 (s, 2H), 3.82 (t, 2H, J=7.6 Hz), 2.81 (t, 2H, J=7.6 Hz).

$^{13}$C NMR (CDCl$_3$, 300 MHz): δ168.0, 141.4, 138.2, 134.3, 132.9, 131.8, 128.2, 127.7, 127.2, 123.5, 118.3, 112.2, 48.2, 36.6, 23.0.

MS (FAB+): m/e 357 ([M+H]+).

| Elemental Analysis: | | | |
|---|---|---|---|
| Calculated: | C 70.78 | H 4.53 | N 15.72 |
| Found: | C 70.30 | H 4.52 | N 15.43 |

Preparative Example 10

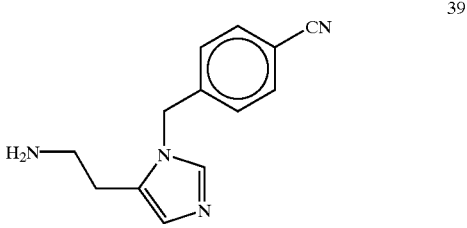

A solution of Compound (38) (21 g, 0.059 mol, 1.0 eq.) and hydrazine monohydrate (15 ml, 0.884 mol, 15.0 eq.) in absolute ethanol (250 ml) was stirred at 50° C. under a nitrogen atmosphere for 12 h. The snow-white suspension was cooled to room temperature and chilled in a refrigerator at −20° C. for one hour. The precipitate (phthalyl hydrazide) was filtered off and thoroughly washed with ice-cold ethanol (190 proof, 500 ml). The filtrates were combined and concentrated under vacuum at 30° C. The residue was subjected to flash column chromatography (CH$_2$Cl$_2$:2 N NH$_3$/MeOH=90: 10 v/v) over silica gel to give N$^\pi$-(4-cyanobenzyl) histamine (39) (11.4 g, 0.050 mol, 85%) as a thick, light-brown oil.

$^1$H NMR (CDCl$_3$, 200 MHz): δ7.64 (d, 2H, J=8.3 Hz), 7.53 (s, 1H), 7.12 (d, 2H, J=8.3 Hz), 6.94 (s, 1H), 5.20 (s, 2H), 2.89 (t, 2H, J=6.8 Hz), 2.54 (t, 2H, J=7.6 Hz), 1.37 (br. s, 2H).

$^{13}$C NMR (CDCl$_3$, 300 MHz): δ141.9, 137.8, 132.9, 132.8, 129.6, 127.7, 127.0, 118.3, 112.1, 47.9, 40.8, 28.0.

MS (FAB+): m/e 227 ([M+H]+).

HR-MS (FAB):

Calculated for $C_{13}H_{15}N_4$ ([M+H]+): 227.1294. Found: 227.1297.

Preparative Example 11

Step A

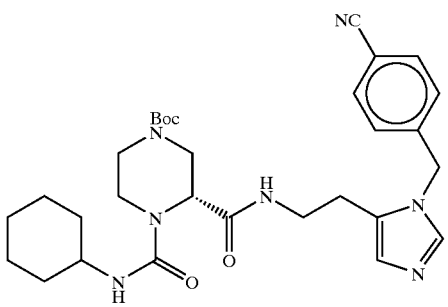

40.1

A solution of Compound (39) (1.50 g, 6.63 mmol, 1.0 eq.) in anhydrous dichloromethane (30 ml) was added drop wise over a period of 30 minutes to a stirred solution of anhydride (32) (2.04 g, 7.95 mmol, 1.2 eq.) in anhydrous dichloromethane (30 ml) at room temperature. A stream of nitrogen was bubbled through the solution to expel evolved carbon dioxide. The colorless solution was stirred for one hour amid nitrogen bubbling. Bubbling was terminated and cyclohexyl isocyanate (1.75 ml, 13.26 mmol, 2.0 eq.) was added drop wise over a period of 5 minutes. The brown solution was stirred at room temperature for one hour to give the Boc protected piperazine intermediate (40.1) (confirmed by $^1$H NMR) which was reacted further without purification in Step B below.

Step B

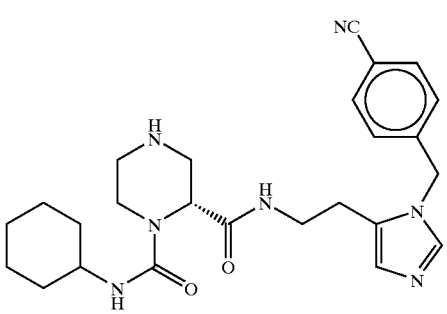

40

The solution mixture containing Compound (40.1) from Step A, above, was concentrated under vacuum at 30° C. The residue was then taken up in a mixture of trifluoroacetic acid (30 ml) and anhydrous dichloromethane (30 ml) and stirred at ambient temperature under a nitrogen atmosphere for 24 h. The mixture was concentrated under vacuum at 30° C. The residual light-brown oil was taken up in 1 N aqueous NaOH solution (100 ml) and extracted with dichloromethane (4×25 ml). The combined organic extracts were washed with brine (25 ml), dried over $Na_2SO_4$, filtered, and concentrated under vacuum at 30° C. The resulting oil was flash-chromatographed ($CH_2Cl_2$:2 N $NH_3$/MeOH=90:10 v/v) over silica gel to give Compound (40) (1.34 g, 2.95 mmol, 45%) as a light-yellow foam.

$^1$H NMR (CDCl$_3$, 200 MHz): δ7.97 (br. s, 1H), 7.65 (d, 2H, J=8.3 Hz), 7.52 (s, 1H), 7.14 (d, 2H, J=8.3 Hz), 6.90 (s, 1H), 5.40 (d, 2H, J=6.8 Hz), 5.21 (s, 2H), 4.28 (d, 1H, J=2.6Hz), H 3.9–1.0 (m, 21H).

MS (FAB+): m/e 464 ([M+H]$^+$).

HR-MS (FAB):

Calculated for $C_{25}H_{34}N_7O_2$ ([M+H]$^+$): 464.2774. Found: 464.2768.

Preparative Example 12

Step A

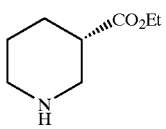

41

Ethyl nipecotate (70.2 g, 0.446 mmol) and D-tartaric acid (67.0 g, 1.0 eq.) were dissolved in hot 95% EtOH (350 mL). The resulting solution was cooled to room temperature, filtered, and the crystals washed with ice-cold 95% EtOH. The product was then recrystallized from 95% EtOH (550 mL) to give ethyl (S)-nipecotate D-tartrate (38.5 g, 56% yield). The salt (38.5 g) was dissolved in water (300 mL), cooled to 0° C., and 3M NaOH was added until the pH was 9-10. The resulting solution was extracted with $CH_2Cl_2$ (5×100 mL) and the combined organics dried over $Na_2SO_4$, filtered, and concentrated under reduced pressure to give Compound (41) as a clear oil (19 g, 89% yield). CIMS: MH$^+$=158.

Step B

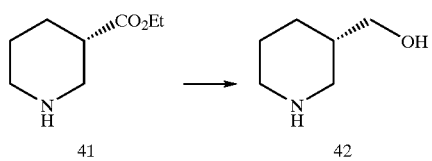

To a solution of Compound (41) from Step A (18.5 g, 0.125 mol) in THF (250 mL) was added LAH (118 mL, 1.0 M in Et$_2$O, 1.0 eq.) at 0° C. over 20 minutes. The resulting solution was warmed to room temperature, then to reflux and stirred 2 hours. The reaction mixture was recooled to room temperature and quenched by the slow addition of saturated $Na_2SO_4$. The resulting slurry was dried by the addition of $Na_2SO_4$, diluted with EtOAc (250 mL), filtered through a plug of Celite, and concentrated to give Compound (42) as a colorless oil (13.7 g 100% crude yield) which was used without purification. CIMS: MH$^+$=116; $[\alpha]^{20}_D$=−8.4° (5.0 mg in 2.0 mL MeOH).

Step C

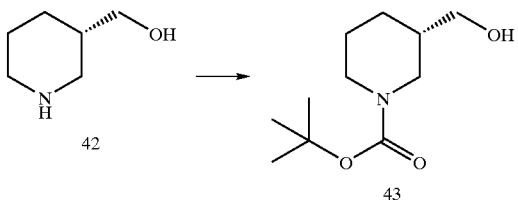

Compound (42) from Step B above (13.6, 0.104 mmol) was dissolved in MeOH (100 mL) and H$_2$O (100 mL). Di-tert-butyl dicarbonate (27.2 g, 1.2 eq.) was added portion wise keeping the pH>10.5 by the addition of 50% NaOH. The resulting solution was stirred at room temperature for 2.5 hours. The reaction mixture was concentrated in vacuo, diluted with H$_2$O (300 mL) and extracted with CH$_2$Cl$_2$ (3×150 mL). The combined organics were dried over Na$_2$SO$_4$, filtered, and concentrated under reduced pressure. The crude product was purified by flash chromatography eluting with 50% EtOH in hexane (12.1 g, 48% yield). CMS: 216 (MH$^+$=100); $[\alpha]^{20}_D$=+15.2° (5.0 mg in 2.0 mL MeOH).

Step D

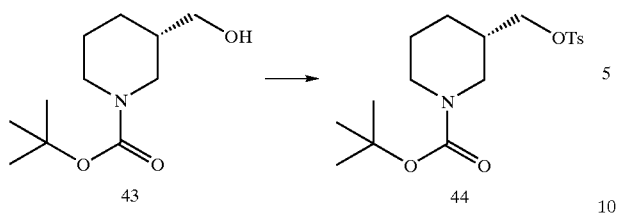

pTosCl (12.8 g, 1.2 eq.) was added portion wise to Compound (43) from Step C (12.0 g, 55.7 mmol) in pyridine (120 mL) at 0° C. The resulting solution was stirred 0° C. overnight. The reaction mixture was diluted with EtOAc (300 mL) and washed with cold 3N HCl (5×300 mL), saturated NaHCO$_3$ (2×150 mL), H$_2$O (1×100 mL), brine (1×100 mL), dried over Na$_2$SO$_4$, filtered, and concentrated in vacuo to give Compound (44) as a pale yellow oil which was used without purification (100% crude yield). FABMS: MH$^+$=370.

Step E

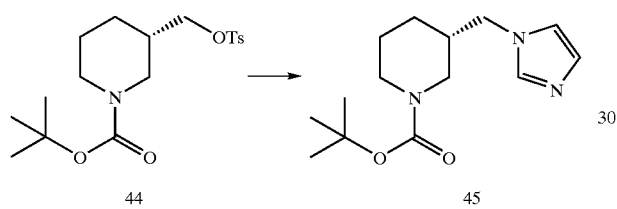

Compound (44) from Step D above (21.0 g, 5.7 mmol) in DMF (300 mL) was treated with sodium imidazole (8.37 g, 1.5 eq.). The resulting solution was stirred, heated to 60° C., and stirred 2 hours. The reaction mixture was cooled to room temperature and concentrated in vacuo. The residue was diluted with H$_2$O (300 mL) and extracted with CH$_2$Cl$_2$ (3×150 mL). The combined organics were dried over Na$_2$SO$_4$, filtered, and concentrated under reduced pressure. The crude product was purified by flash chromatography using a 7% MeOH in CH$_2$Cl$_2$ solution as eluent to give Compound (45) as a pale yellow solid (7.25 g, 49% yield). FABMS: MH$^+$=266; $[\alpha]^{20}_D$=+8.0° (5.0 mg in 2.0 mL MeOH).

Step F

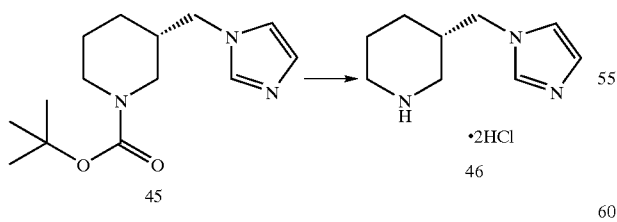

The title compound (45) from Step E (5.50 g, 20.7 mmol) was stirred at room temperature in 4M HCl/dioxane (50 mL) overnight. The resulting solution was concentrated in vacuo and triturated with Et$_2$O to give Compound (46) as a yellow solid. CIMS: MH$^+$=166.

Preparative Example 13

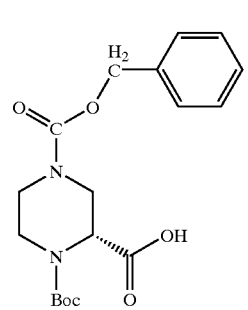

2-Carboxy-piperazine-dicamphorsulfonic acid salt (30) (Preparative Example 1) (17.85 gm, 30 mmole) was dissolved in 180 ml of distilled water. Dioxane (180 mL) was added and the pH adjusted to 11.0 with 50% NaOH. The reaction mixture was cooled to 0–5° C. in an ice-MeOH bath and a solution of benzyl-chloroformate (4.28 mL, 30 mmol) in 80 mL of dioxane was added over a period of 30–45 minutes while stirring at 0–5° C. and keeping the pH at 10.5 to 11.0 with 50% NaOH. After the addition was complete, stirring was continued for 1 hr. The reaction mixture was then evaporated to dryness (to get rid of the dioxane for extraction). The residue was dissolved in 180 mL of distilled water and the pH adjusted slowly to 4.0 with 1N HCl. The aqueous solution was washed with 3×180 mL of ethyl acetate (The ethyl acetate was dried over MgSO$_4$, filtered, and evaporated to obtain N,N-di-CBZ-2-carboxy-piperazine and saved). The pH of the aqueous layer, which contains the desired product, was adjusted to 10.5 to 11.0 with 50% NaOH and solid di-tert-butyl-dicarbonate (7.86 gm, 36 mmol) was added and the mixture was stirred while keeping the pH at 10.5 to 11.0 with 50% NaOH. After 1 hr. the pH stabilized. When the reaction was complete, the reaction mixture was washed with 2×180 mL of Et$_2$O. The aqueous layer was cooled in an ice bath and the pH was adjusted to 2.0 with 1N HCl (slowly). The reaction mixture was extracted with 3×200 mL of ethyl acetate, dried over MgSO$_4$, filtered and concentrated to obtain 9.68 gm (88%) of pure product (47) as a white solid.

Preparative Example 14

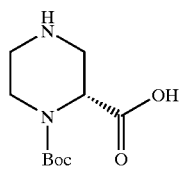

Compound (47) from Preparative Example 13 (9.6 gm, 26.3 mmol) was dissolved in 100 mL of absolute ethanol in a hydrogenation vessel. The vessel was flushed with nitrogen and 3 gm of 10% Pd/C (50% by weight with water) was added. The mixture was hydrogenated at 55 psi of H$_2$ for 18 hours. After 18 hrs, the reaction mixture had a precipitate. The TLC was checked (30% MeOH/NH$_3$/CH$_2$Cl$_2$). The reaction mixture was filtered on a pad of Celite, and the pad washed with EtOH followed by distilled water. The filtrate was evaporated to ~⅓ the volume (to get rid of the EtOH) and 200 mL of distilled water was added. The aqueous layer was extracted with ethyl acetate three times (the ethyl acetate layer containing pure N,N-Di-Boc-2-carboxy-piperazine was saved). The water layer was evaporated to dryness and evaporated from methanol two times to obtain 3.98 gm of pure product (48).

Preparative Example 15
Step A

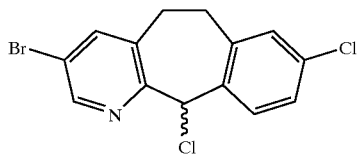

49

The tricyclic alcohol (Preparative Example 40 in WO 95/10516)(5.6 gm, 17.33 mmol) was dissolved in 56 ml of dichloromethane and 2.46 ml of thionyl chloride was added while stirring under a dry nitrogen atmosphere. After 5 hours the TLC was checked (by adding an aliquot of the reaction mixture to 1N NaOH and shaking with dichloromethane and checking the dichloromethane layer by TLC using 50% EtOAc/Hexanes as the eluent). The mixture was evaporated to give a gum, which was evaporated, twice from dry toluene and once from dichloro-methane to give the 11-chloro derivative (49) as a foamy solid, which was used without further purification.

Step B

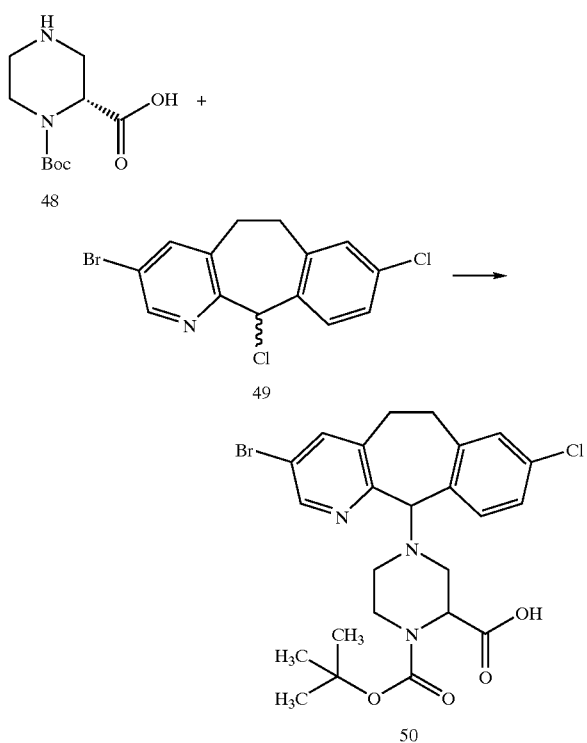

Compound (49) from Step A above, was dissolved in 100 ml of dry DMF, and Compound (48) from Preparative Example 14 (3.98 gm) was added followed by 12.11 ml of triethylamine. The mixture was stirred at ambient temperature under a nitrogen atmosphere. After 24 hours the DMF was evaporated and the residue dissolved in 200 ml of ethyl acetate and washed with brine. The brine layer was washed with ethyl acetate two more times and the ethyl acetate layers combined, dried over magnesium sulfate, filtered, and evaporated to give a foamy solid. The solid was chromatographed on a 1½"×14" column of silica gel eluting with 2 L of 0.4% 7N MeOH/NH$_3$:CH$_2$Cl$_2$, 6 L of 0.5% 7N MeOH/-NH$_3$:CH$_2$Cl$_2$, 2 L of 0.65% 7N MeOH/NH$_3$:CH$_2$Cl$_2$, 2 L of 0.8% 7N MeOH/NH$_3$:CH$_2$Cl$_2$, 4 L of 1% 7N MeOH/NH$_3$:CH$_2$Cl$_2$, 2 L of 3% 2N MeOH/NH$_3$:CH$_2$Cl$_2$, 2 L of 5% 2N MeOH/NH$_3$:CH$_2$Cl$_2$, 2 L of 10% 2N MeOH/NH$_3$:CH$_2$Cl$_2$, 2 L of 15% 2N MeOH/NH$_3$:CH$_2$Cl$_2$, 4 L of 20% 2N MeOH/NH$_3$:CH$_2$Cl$_2$ to obtain 4.63 gm of final product (50).

Preparative Example 16

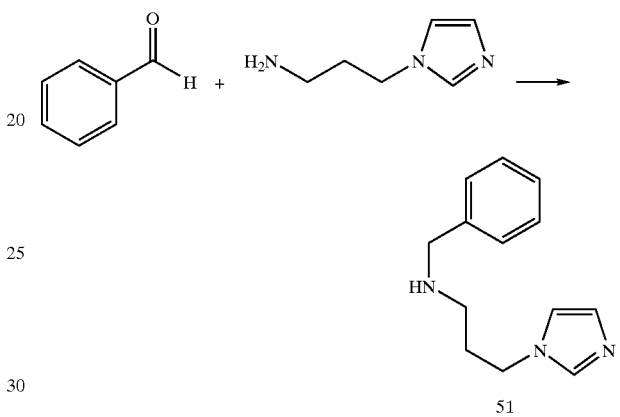

51

A mixture of 1-(3-aminopropyl)imidazole (37.1 g, 297 mmol), benzaldehyde (30 g, 283 mmol), 3 Å molecular sieves (50 g), sodium acetate (24.1 g, 283 mmol) and anhydrous methanol (700 mL) was stirred at room temperature under N$_2$ overnight. The mixture was cooled to 0° C. and sodium borohydride (10.9 g, 288 mmol) was added portion wise over 1 hour. The mixture was stirred at room temperature for 3 hours. The mixture was filtered through celite, washed with methanol, and concentrated in vacuo to give a residue, which was diluted with dichloromethane and washed with 10% aqueous sodium hydroxide. The organic phases were washed with brine, dried over anhydrous magnesium sulfate, filtered and concentrated in vacuo to give the title compound as a pale yellow oil (56.3 g, 92%, MH$^+$= 216).

Preparative Example 17

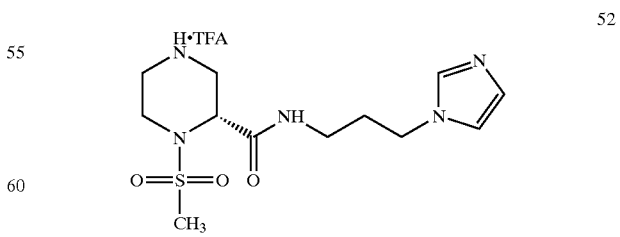

52

In essentially the same manner as Preparative Examples 4 and 5, except substituting methanesulfonyl chloride for cyclohexylisocyanide, Compound (52) was prepared.

Preparative Example 18

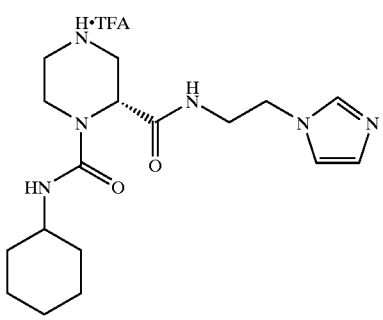
53

In essentially the same manner as Preparative Examples 4 and 5, except substituting 1-(2-aminoethyl)imidazole) for 1-(3-aminopropyl)imidazole), Compound (53) was prepared.

Preparative Example 19

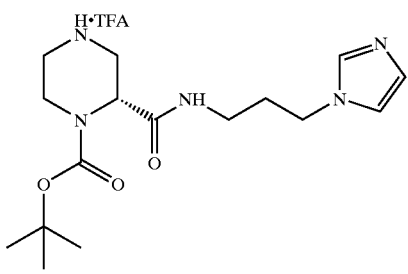
54

Compound (32) from Preparative Example 3 was treated with 1-(3-aminopropyl)imidazole in essentially the same manner as Preparative Example 4 to afford the t-Boc derivative, which was further reacted in a similar manner as in Preparative Example 5 to afford Compound (54).

Preparative Example 20
Step A

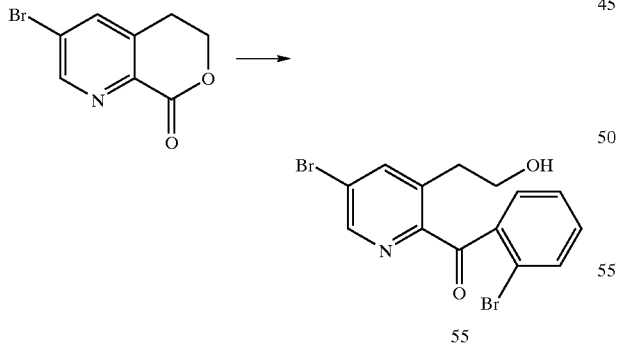
55

To a solution of 1,2-iodobromobenzene (11.5 mL) in 840 ml of tetrahydrofuran, cooled to −78° C. and under a dry nitrogen atmosphere was added 45.5 mL of a 2 M ether solution of isopropylmagnesiumchloride. After stirring for 30 minutes, a solution of 3-bromo-5,6-dihydro-2H-pyrano[3,4-b]pyridin-8-one (14 gm, 61.67 mmol) in 100 mL of tetrahydrofuran was added and the reaction mixture stirred for 1 hr. The reaction was then poured into a solution of saturated ammonium chloride and the resulting mixture extracted three times with ethyl acetate. The combined ethyl acetate layers were then dried over magnesium sulfate, filtered, and evaporated to give a solid. The solid was crystallized from ethylacetate/hexanes to obtain 21.82 g of compound (55) FABMS M+1=384.

Step B

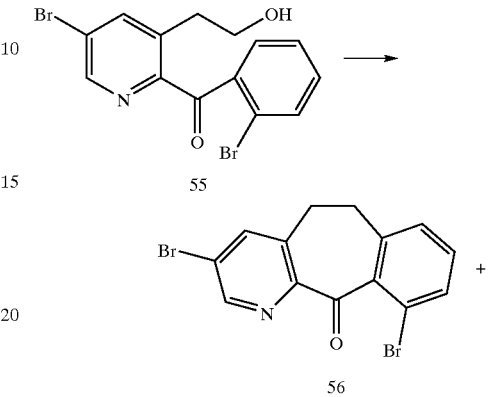

Compound (55) from Step A (15 gm, 39 mmol) was mixed with 67 gm of aluminum chloride and the mixture was heated to 160° C. in a round bottom flask for 2 hours. While cooling the reaction in an ice bath, ice, followed by 500 ml of water was added. Sodium hydroxide(50%) was added to adjust the pH to 12. The resulting solution was extracted three times with ethyl acetate to obtain 9.75 gm of a crude mixture of products which was further purified by chromatography to obtain 1.25 gm of compound (56) FABMS M+1=365.

Step C

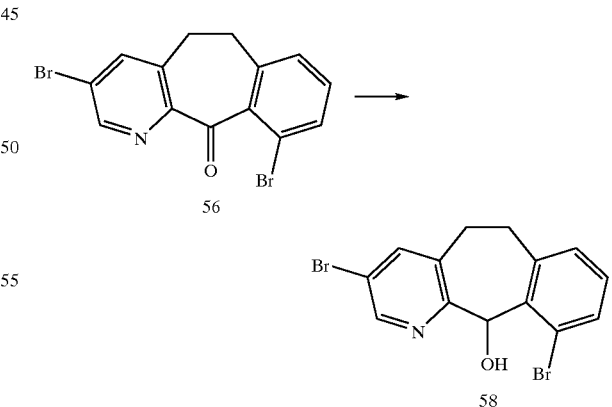

To a solution of Compound (56) from Step B (1.2 gm, 3.3 mmol) in 20 ml of methanol at room temperature was added, portion wise, sodium borohydride (0.29 gm, 5 mmol). After 1 hour, 30 ml of 1N hydrochloric acid was added and the mixture stirred for 5 minutes. To the reaction was added, 1N sodium hydroxide (50 ml) and the resulting mixture extracted with dichloromethane to obtain 1.18 gm of title compound which was used directly in the next step without further purification FABMS M⁺1=367.

Step D

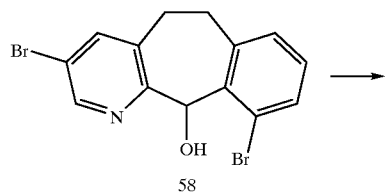

58

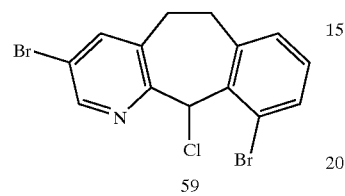

59

Compound (58) from Step C, was treated in a manner similar to that described in Preparative Example 15, Step A, to obtain compound (59)

Preparative Example 21

Step A Preparation of Compound (60).

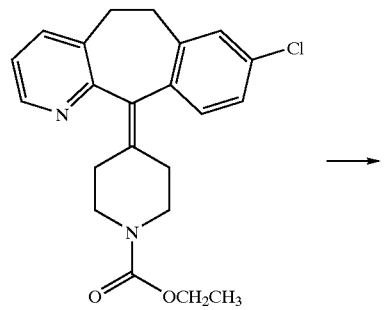

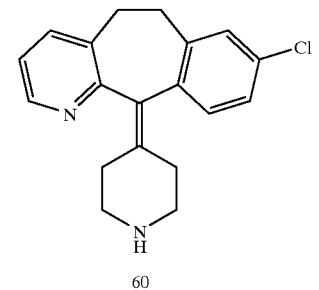

60

Loratadine® (448 g, 1.17 mol) was refluxed in 2 L of 70% aqueous HCl (1.4 L conc.HCl in 600 ml H$_2$O) for 12 h. The reaction mixture was then cooled and poured into ice. It was then basified with 950 mL of 50% NaOH followed by extraction with CH$_2$Cl$_2$ (1×4 L, and 2×2.5 L). The organic phase was washed with brine, dried over Na$_2$SO$_4$ and MgSO$_4$ and then filtered. All the volatiles were then removed to give 368 g of the title compound (60). MH⁺=311

Step B Preparation of Compound (61).

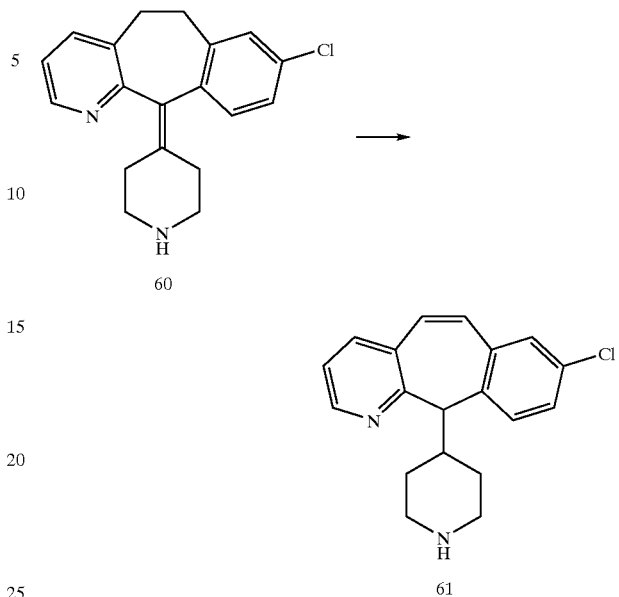

To the title compound from Preparative Example 21, Step A (363 g, 1.17 mol) was added trifuromethane sulfonic acid (1.8 Kg) under N$_2$. The reaction mixture was refluxed at 170° C. The progress of the reaction was monitored by $^1$H NMR. After 4 days the reaction was only 63% complete. After 8 days the reaction was found to be 80% complete according to $^1$H NMR; thus another 130 mL of CF$_3$SO$_3$H was added and refluxing continued for another 24 h. It was then poured into ice and basified with 800 mL of NaOH (50%) and extracted twice with CH$_2$Cl$_2$ (1×8 L then 1×7 L). The organic phase was combined, washed with H$_2$O and filtered through celite. It was then dried over MgSO$_4$ and Na$_2$SO$_4$ and again filtered through celite. The filtrate was concentrated to give a black brown semi-solid that was pre-adsorbed on 600 g of silica gel and then chromatographed on 2.3 Kg of silica gel eluting first with 5% CH$_3$OH—CH$_2$Cl$_2$ (saturated with ammonia) and then with 10% CH$_3$OH—CH$_2$Cl$_2$ (saturated with ammonia) to give 102 g of the title compound (61) as a solid. mp=73–75; MS (FAB) m/z 483 (MH⁺).

Step C Preparation of Compound (62)

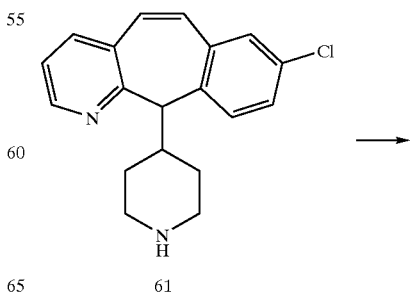

61

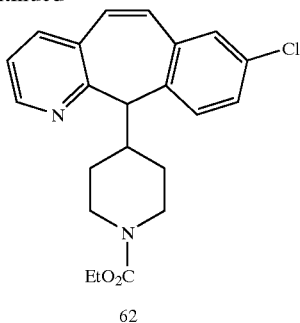

62

To a solution of the title compound of Preparative Example 21, Step B (145 g) in 1 L of CH$_2$Cl$_2$ at 0° C. was added ethylchloroformate (55 mL), dropwise. The reaction mixture was stirred at room temperature overnight. It was further diluted with 1 L CH$_2$Cl$_2$ and stirred with 2 L of dilute NaHCO$_3$, pH~7–8. The organic layer was separated and dried over MgSO$_4$ and Na$_2$SO$_4$, filtered and concentrated to afford 174 g of a brown black gum. The crude compound was purified by silica gel column chromatography, eluting with 20–60% ethyl acetate-hexane to afford the title compound (62). MS (FAB) m/z 383 (MH$^+$).

Step D Preparation of compounds (63) and (64)

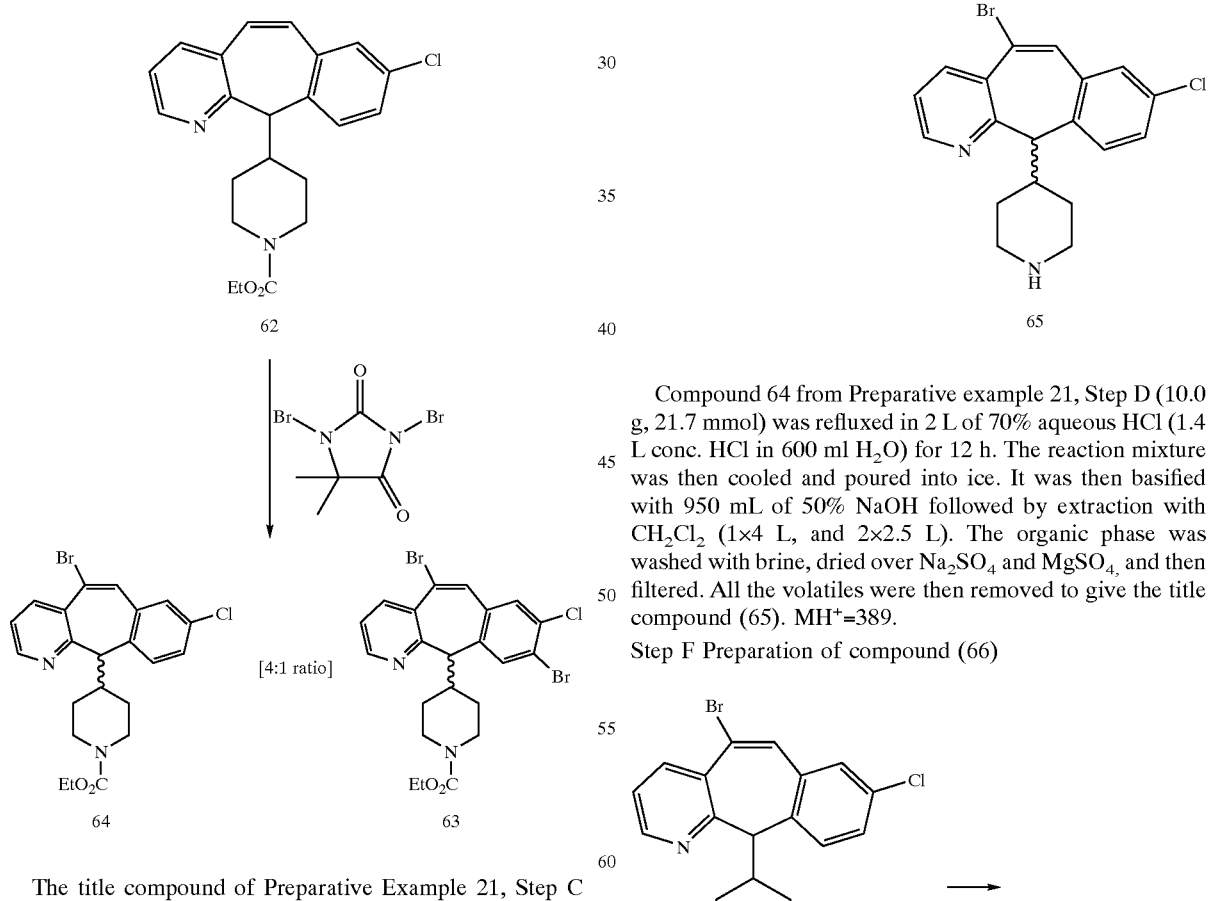

The title compound of Preparative Example 21, Step C (251 g, 0.65 mol) was dissolved in 1.65 L of CH$_2$Cl$_2$ and dibromo-dimethylhydantoin (132 g, 0.462 mol) was then added. The solution was stirred until the system was homogeneous. The solution was cooled to 0° C. under N$_2$ atmosphere and 174 mL of CF$_3$SO$_3$H was added over 37 min. while keeping temperatures between $^-$1° C. to $^+$1° C. The reaction mixture was stirred for 3 h, cooled to $^-$10° C. and basified with 50% NaOH (170 mL), keeping the temperature below $^+$1° C. The aqueous phase was extracted with CH$_2$Cl$_2$ and then dried over MgSO$_4$ and concentrated to give 354 g of yellow foam that was chromatographed on silica gel eluting with 10–50% of ethyl acetate-hexanes gradient to give 50 g of compound (63) (14% yield) and 147 grams of the desired title compound (64) (49% yield). Compound (64) MS m/z (rel intens) 462 (MH$^+$); Compound (63) MS m/z (rel intens) 542 (MH$^+$).

Step E Preparation of Compound (65)

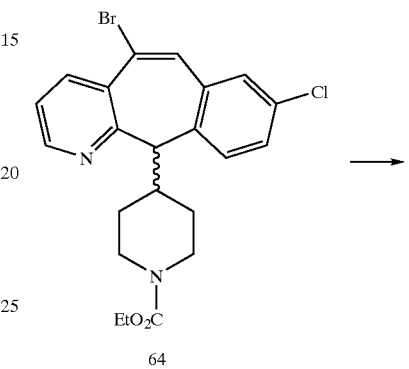

64

Compound 64 from Preparative example 21, Step D (10.0 g, 21.7 mmol) was refluxed in 2 L of 70% aqueous HCl (1.4 L conc. HCl in 600 ml H$_2$O) for 12 h. The reaction mixture was then cooled and poured into ice. It was then basified with 950 mL of 50% NaOH followed by extraction with CH$_2$Cl$_2$ (1×4 L, and 2×2.5 L). The organic phase was washed with brine, dried over Na$_2$SO$_4$ and MgSO$_4$, and then filtered. All the volatiles were then removed to give the title compound (65). MH$^+$=389.

Step F Preparation of compound (66)

65

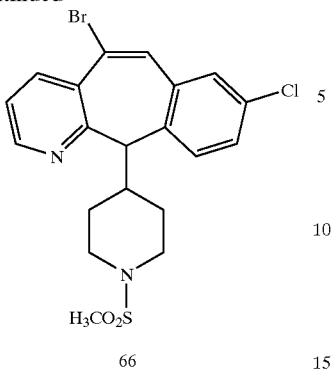

To a solution of the amine product (65) from Preparative Example 21, Step E (20.0 g) in CH$_2$Cl$_2$ (100 ml) was added triethyl amine (14.4 ml). Slowly, methane sulfonyl chloride (6.0 ml) was added and the mixture stirred over night at room temperature. To the reaction was added saturated sodium bicarbonate and then it was extracted with CH$_2$Cl$_2$. The organic layer was dried over magnesium sulfate, filtered and concentrated to dryness. The crude product mixture was purified with column chromatagraphy, eluting with 1% MeOH/NH$_3$—CH$_2$Cl$_2$, to afford the desired compound (66). MS 469 (MH$^+$).

Step G Preparation of Compound (67) and (68)

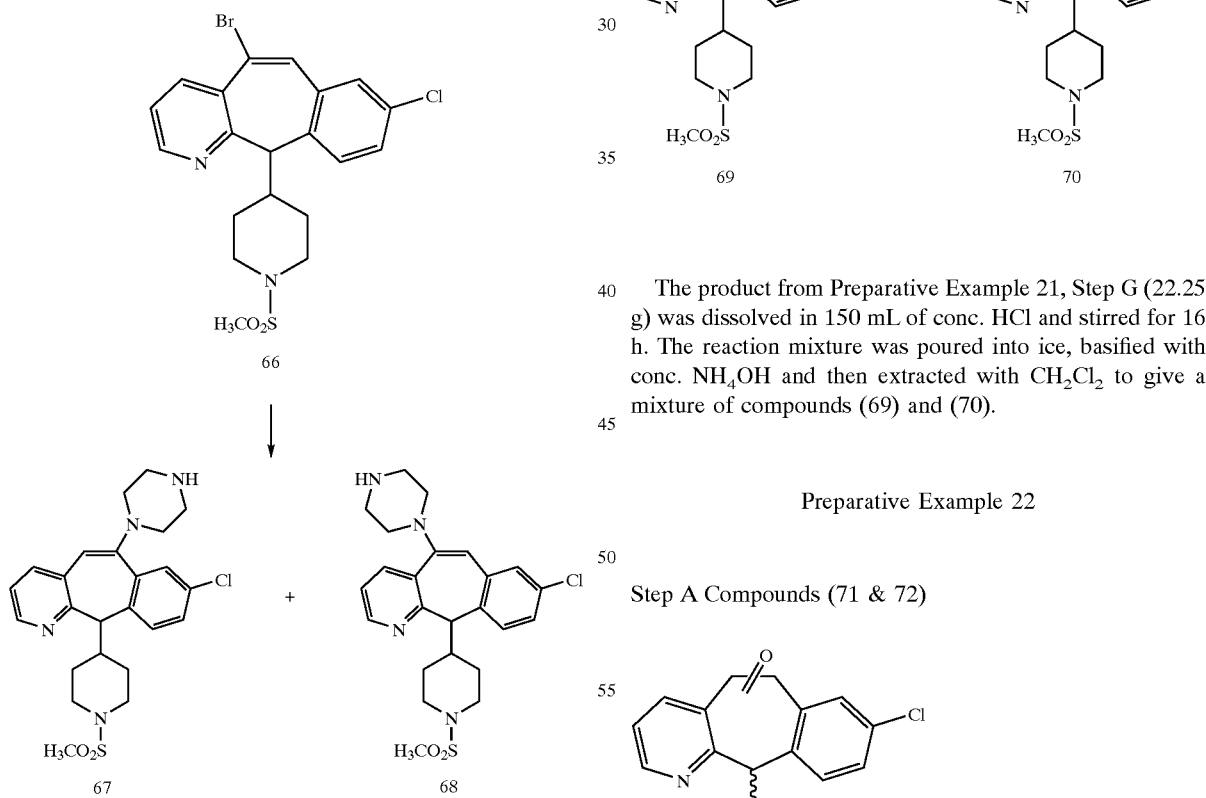

To the title compound from Preparative Example 21, Step F (21.25 g, 45.3 mmol, 1 eq.) in 400 mL of THF was added 19.5 g (266.6 mmol, 5 eq.) of piperazine. The reactants stirred at room temperature until everything was in solution. To this mixture was added potassium t-butoxide 12.7 g (113.3 mmol, 2.5 eq.) in one portion. The reaction mixture was stirred at room temperature for 2 h. All of the THF was removed by rotary evaporation and the resulting crude product was extracted with EtoAc and washed with water. The organic layer was dried over Na$_2$SO$_4$ and concentrated to give a mixture of title compounds (67) and (68).

Step H Preparation of Compound (69) and (70)

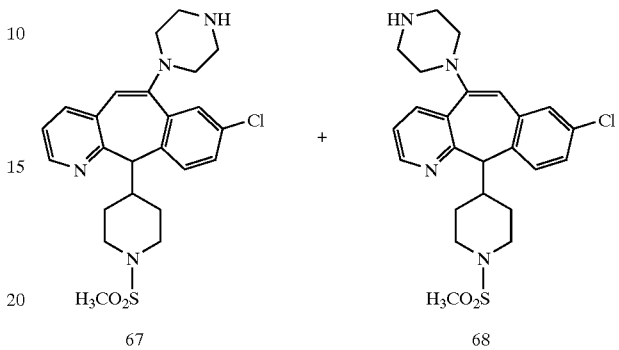

The product from Preparative Example 21, Step G (22.25 g) was dissolved in 150 mL of conc. HCl and stirred for 16 h. The reaction mixture was poured into ice, basified with conc. NH$_4$OH and then extracted with CH$_2$Cl$_2$ to give a mixture of compounds (69) and (70).

Preparative Example 22

Step A Compounds (71 & 72)

-continued

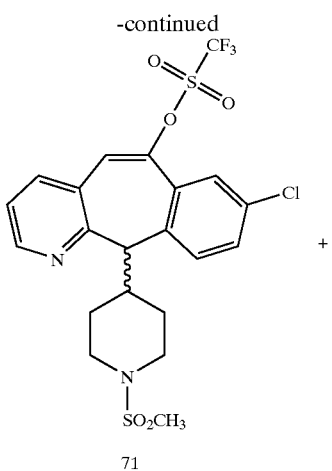

71

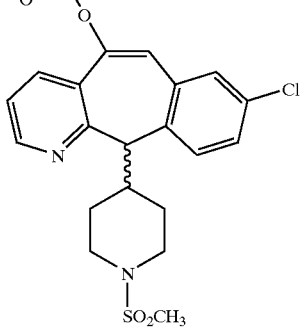

72

To a mixture of piperazinyl compounds 69 & 70, from Preparative Example 21, Step H in THF (150 mL) at −78° C. was added LDA 4.05 mL (1.1 eq.) and the solution stirred for 1.5 h. The mixture was warmed to −20° C. and then N-phenyl trifluoromethane sulfonimide 2.94 g (1.1 eq.) was added. The reaction stirred over night at room temperature. After all of the THF was removed by rotatary evaporation, the resulting crude product was purified by Biotage column chromatography eluting with 50% EtoAc-Hex, (normal phase) to yield 1.94 g of the desired compound (71).

Step B Preparation of Compound (73)

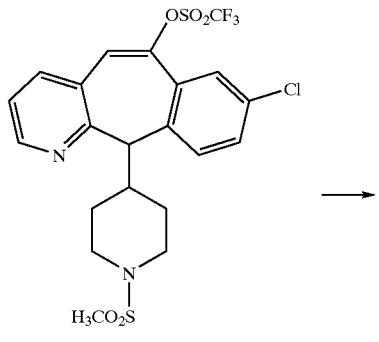

71

-continued

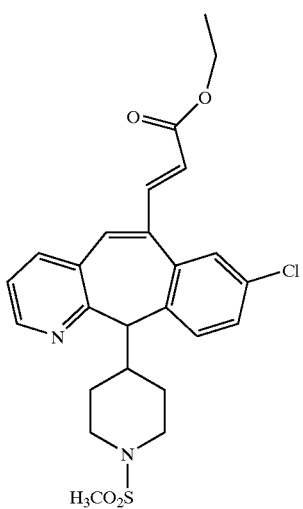

73

Compound (71) from Preparative example 22, Step A above, was dissolved in DMF. Successively, $Et_3N$ (29 eq.), Ethyl acrylate (5.4 eq.), $K_2CO_3$ (5 eq.), $Bu_4NBr$ (2 eq.) and Palladuim (II) acetate (0.13 eq.) were added. The mixture was stirred and heated to 100° C. for 4 h. After cooling, the mixture was concentrated and the residue was taken up in $CH_2Cl_2$ and extracted with $CH_2Cl_2/H_2O$. The organic layer was dried over $Na_2SO_4$ then concentrated and the residue purified by Biotage chromatography using 1% MeOH/ $NH_3$—$CH_2Cl_2$ to afford the title compound (73).

Step C Preparation of Compound (74)

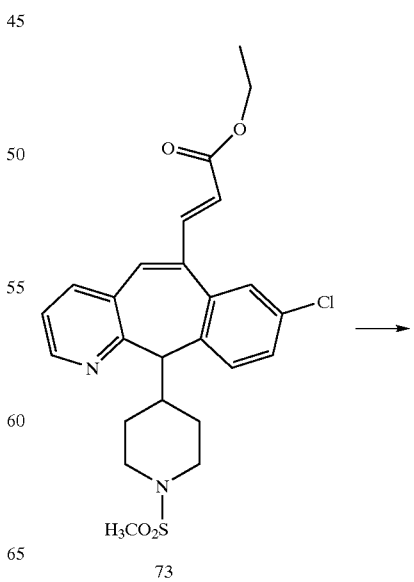

73

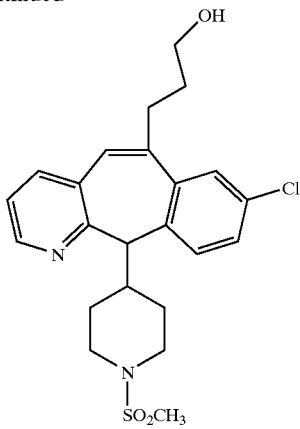

74

Compound (73) was dissolved in EtOH, cooled in an ice bath and reacted with NaBH₄ (15 eq.) for 3 min. Then CuCl (2 eq) was added and the reaction mixture was stirred for 6 h. at room temperature. The mixture was filtered, concentrated and extracted with CH₂Cl₂. The organic layer was washed with sat. NaHCO₃, dried over Na₂SO₄ and concentrated to yield the title compound (74).

Step D Preparation of Compound 75

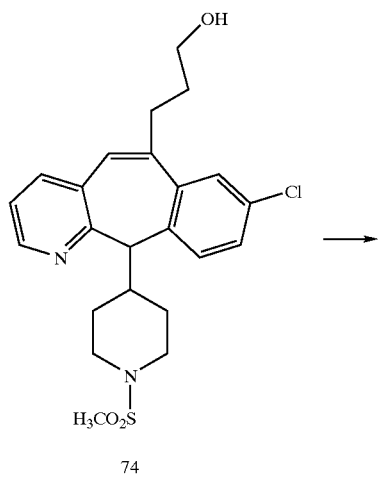

74

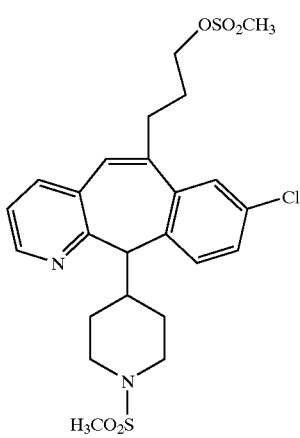

75

To a solution of Compound 74 (1.24 g) in CH₂Cl₂ (100 ml) was added triethyl amine (1.1 ml). Slowly, methane sulfonyl chloride (0.3 ml) was added and the mixture stirred over night at room temperature. To the reaction was added saturated sodium bicarbonate and then it was extracted with CH₂Cl₂. The organic layer was dried over magnesium sulfate, filtered and concentrated to dryness. The crude product mixture was purified with column chromatography, eluting with 80% EtOAc-Hex, to afford the title compound (75).

Preparative Example 23

Step A Preparation of Compound 78

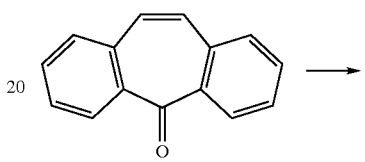

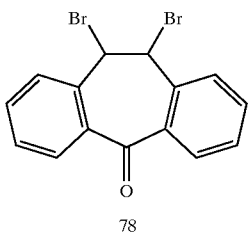

78

To a stirred solution of bromine (33.0 g, 210 mmol) in CCl₄ (100 ml) was added a solution of dibenzosuberenone (37.0 g, 179 mmol) in CCl₄ (200 ml) at room temperature. The resulting solution was stirred at room temperature for 1.5 hours. The white crystals were collected by filtration to give the product (78) (60.12 g, 92% yield, M+H=367).

Step B Preparation of Compound (79)

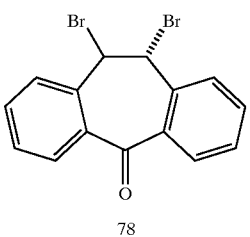

78

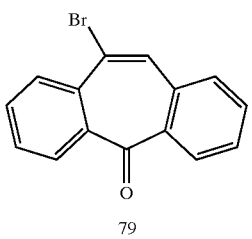

79

A solution of the di-bromo compound (78) (10.0 g, 27.3 mmol) and NaOH (3.0 g, 82.0 mmol) in MeOH (200 ml) was stirred and heated to reflux for 1.5 hours. The reaction mixture was then cooled to room temperature and stirred overnight. The mixture was evaporated to dryness and then extracted with CH$_2$Cl$_2$—H$_2$O. The combined organic layer was dried over MgSO$_4$, filtered and evaporated to dryness to give a white solid (79) (8.0 g, 100% yield, M=285)

Step C Preparation of Compound 80

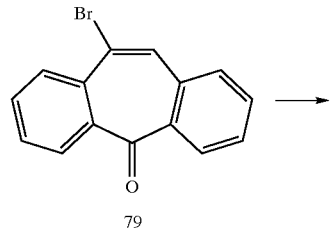

To a stirred solution of the mono-bromo compound (79) from step B (3.9 g, 13.7 mmol) in MeOH (200 ml) under nitrogen and at 0° C. was added NaBH$_4$ (0.7552 g, 20.0 mmol). The resulting solution was stirred at 0° C. for 3 hours, then evaporated, followed by extraction with CH$_2$Cl$_2$—H$_2$O. The combined organic layer was dried over MgSO$_4$, filtered, and evaporated to dryness to give a white solid (80) (4.1 g, 100%, M=287).

Step D Preparation of Compound 81

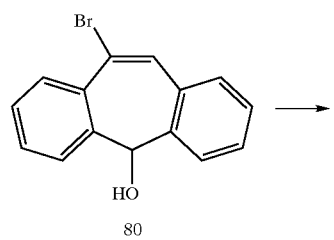

To a stirred solution of alcohol (80) from Preparative Example 3, Step C (3.9 g, 13.6 mmol) in CH$_2$Cl$_2$ (100 mL) under nitrogen at −20° C. was added thionyl chloride (13.9 mL, 1.0 mmol). The resulting solution was stirred at room temperature overnight and then evaporated to dryness. The crude mixture was diluted with toluene (50 mL), followed by the addition of more SOCl$_2$ (13.9 mL) at room temperature. The resulting solution was heated to reflux for 2 hours until the reaction went to completion. The reaction mixture was then cooled to room temperature and concentrated to dryness to give a light brown solid (81) (5.0 g, 100% yield, M−BrCl=191)

Step E Preparation of Compound 82

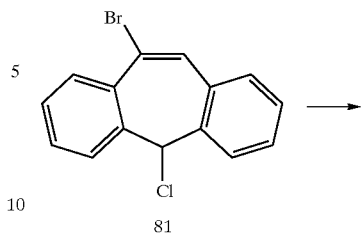

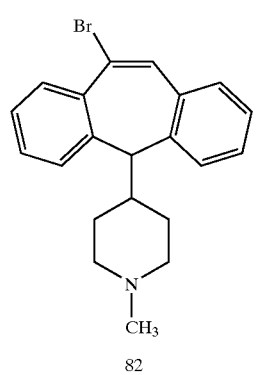

To a suspension of Mg (3.63 g) in anhydrous THF (95 mL) under nitrogen and at room temperature was added 4-chloro-1-methyl piperidine (3 mL, 10% of the total amount) and one small crystal of iodine. The resulting solution was heated to reflux, followed by the addition of iodomethane (0.5 mL) and the remainder of the 4-chloro-1-methyl piperidine (27 mL). The reaction was stirred for one hour and then concentrated to dryness to give the crude Grignard reagent (0.8 M).

To a stirred solution of the chloro compound (81) from Preparative Example 3, Step D (3.9 g, 13.7 mmol) in anhydrous THF (40 mL) under nitrogen at 0° C. was added dropwise the Grignard reagent (obtained above) (0.8M, 19.5 mL, 15.6 mmol). The resulting solution was stirred at 0° C. for 1 hour. The reaction mixture was quenched with 100 mL of 15% aq. NH$_4$Cl solution, followed by the extraction with EtOAc-H$_2$O. The combined organic layer was dried over MgSO$_4$, filtered and evaporated to dryness to give the product (82) (5.29 g, 100% yield, MH$^+$=368).

Step F Preparation of Compound 83

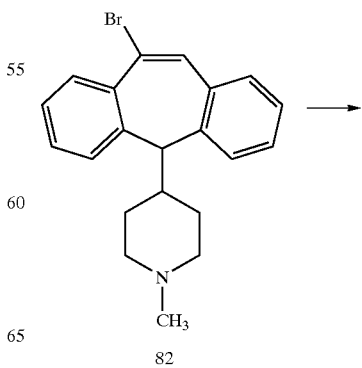

-continued

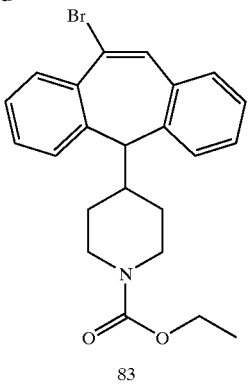
83

To a stirred solution of Compound (82) from Step E above (5.0 g, 13.6 mmol) in toluene (100 mL) under a nitrogen atmosphere, was added triethylamine (5.7 mL, 40.7 mmol). The resulting solution was heated to refux, then dropwise ethyl chloroformate (13.0 mL, 136.7 mmol) was added. The solution continued to stir at the reflux temperature for 2 hours. The reaction was then stirred at room temperature overnight, followed by extraction with an EtOAc-1N NaOH solution. The combined organic layer was dried over MgSO$_4$, filtered, concentrated to dryness and the crude product purified by column chromatography on normal phase silica gel, eluting with 10% EtOAc/90% Hexane to give (83).

Step G Preparation of Compound 84

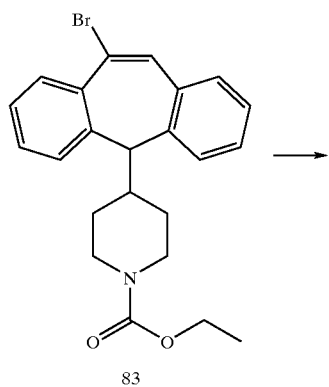
83

The product from Preparative Example 23, Step E was dissolved in 25 mL of conc. HCl and heated to reflux overnight. The reaction mixture was poured into ice basified with 50% w/w NaOH and then extracted with CH$_2$Cl$_2$ to give the desired compound 84.

Step H Preparation of Compound 85

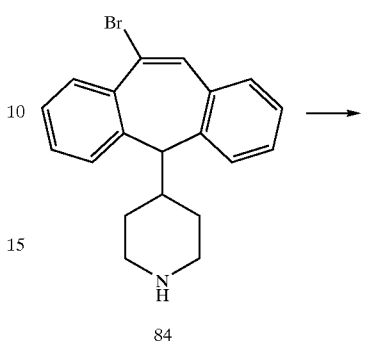
84

To a solution of the amine (84) (0.82 g) in CH$_2$Cl$_2$ (10 ml) was added triethyl amine (1.0 ml). Slowly, methane sulfonyl chloride (0.3 ml) was added and the mixture stirred over night at room temperature. To the reaction was added saturated sodium bicarbonate and then it was extracted with CH$_2$Cl$_2$. The organic layer was dried over magnesium sulfate, filtered and concentrated to dryness to give the desired compound (85).

Step I Preparation of compound 86

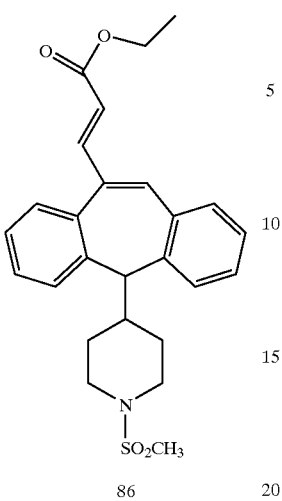

86

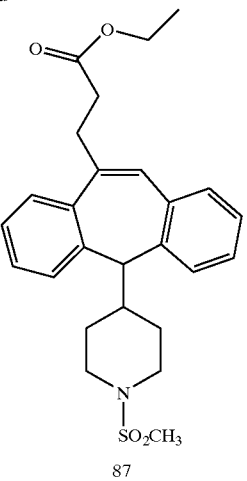

87

Compound (85) from Preparative Example 23 Step H, was dissolved in DMF. Successively, Et₃N (29 eq.), Ethyl acrylate (5.4 eq.), K₂CO₃ (5 eq.), Bu₄NBr (2 eq.) and Palladuim (II) acetate (0.13 eq.) were added. The mixture was stirred and heated to 100° C. for 4 h. After cooling, the mixture was concentrated and the residue was taken up in CH₂Cl₂ and extracted with CH₂Cl₂/H₂O. The organic layer was dried over Na₂SO₄ then concentrated and the residue purified by normal phase silica gel using 25% EtOAc-75% hexane to afford the title compound (86).

Compound (86) from Step I above was dissolved in EtOH, followed by the addition of CH₂Cl₂ at room temperature. To this reaction solution was added 10% w/w of PtO₂ and the reaction stirred at room temperature under H₂ (balloon) overnight. The reaction mixture was filtered through celite and concentrated to yield the title compound 87.

Step K Preparation of Compound 88

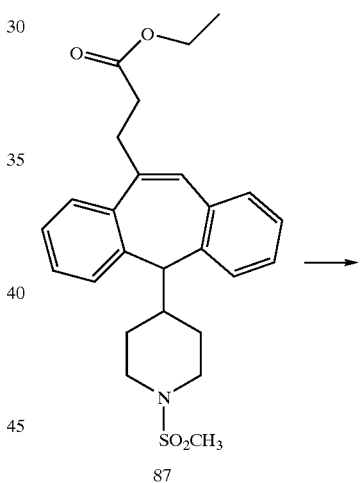

87

Step J Preparation of Compound 87

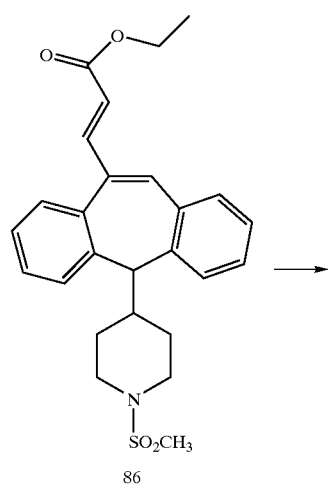

86

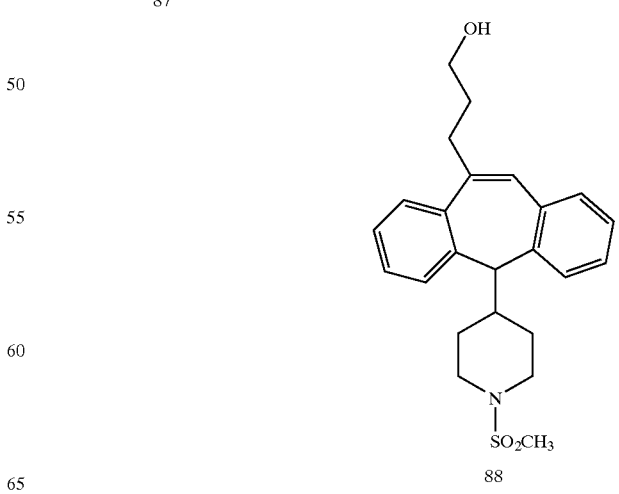

88

To a stirred solution of the ester (87) from Step J above, (0.63 g, 1.4 mmol) in THF (10 mL) at 0° C. was added a 1M solution of DIBAL (2.8 mL, 2.8 mmol). The resulting solution was stirred at room temperature overnight. An additional portion of 1M DIBAL was added and the mixture was stirred for 4 more hours at 0° C. The reaction solution was extracted with EtOAc-10% citric acid, 1N NaOH. The combined organic layer was dried over $Na_2SO_4$ filtered and evaporated to give title compound 88.

Step L Preparation of compound 89.

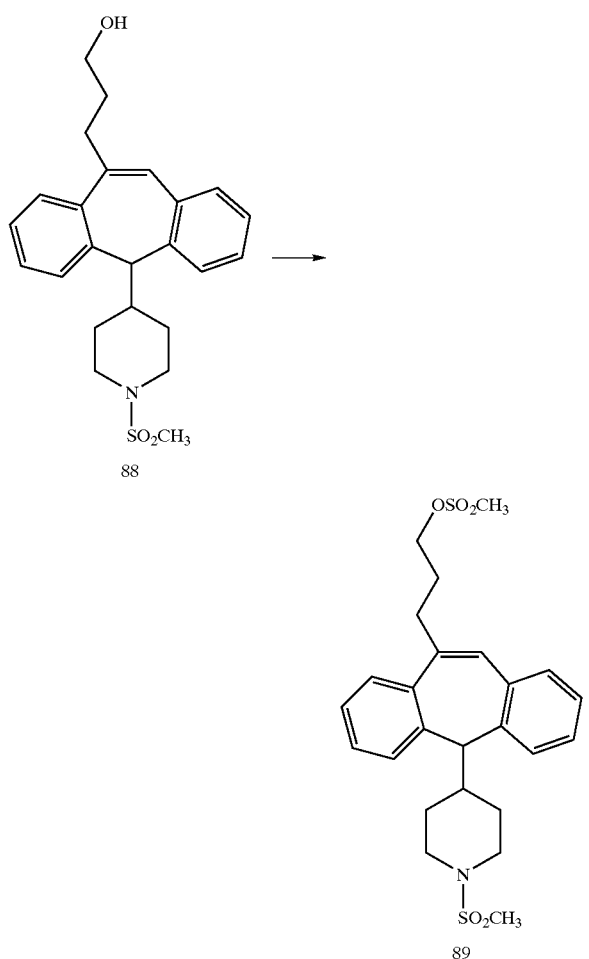

In a similar manner as was described in Preparative example 22, Step D, triethyl amine was added to a solution of Compound (88) in $CH_2Cl_2$ (100 ml). Slowly, methane sulfonyl chloride was added and the mixture stirred over night at room temperature. To the reaction was added saturated sodium bicarbonate and then it was extracted with $CH_2Cl_2$. The organic layer was dried over magnesium sulfate, filtered and concentrated to dryness. The crude product mixture was purified with column chromatography, eluting with 80% EtOAc-Hex, to afford the title compound (89).

Preparative Example 24
Step A Preparation of Compound (90)

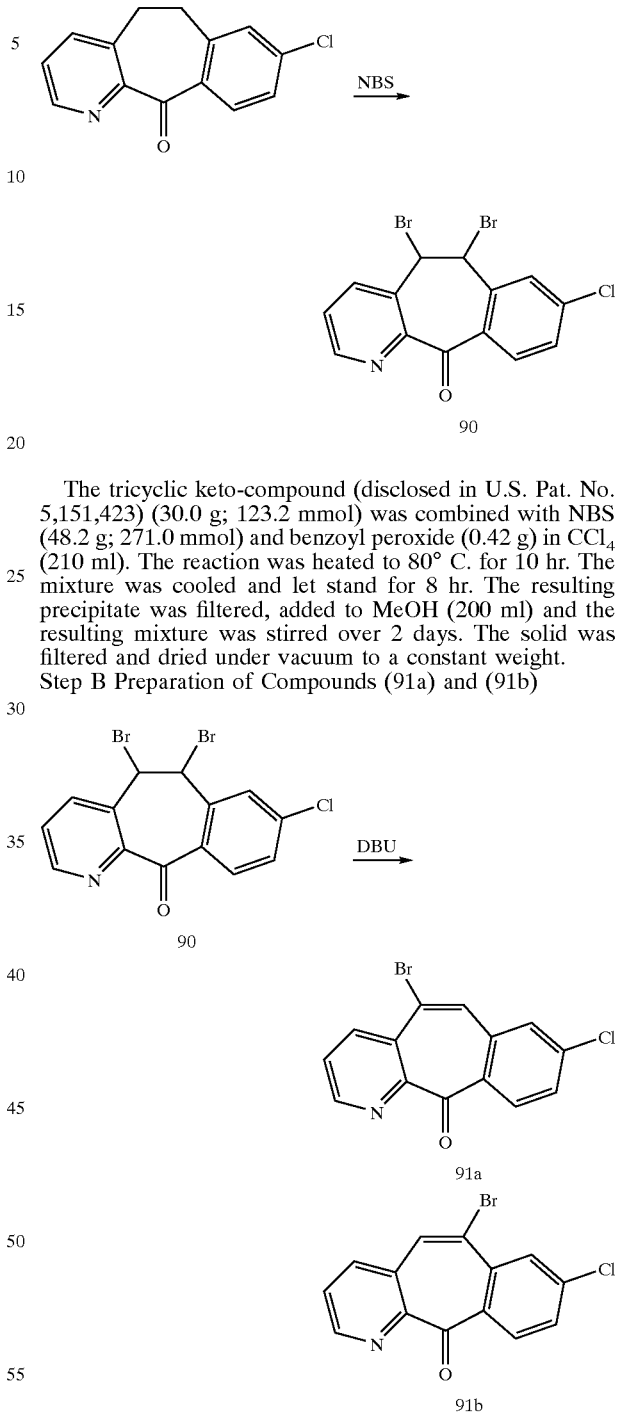

The tricyclic keto-compound (disclosed in U.S. Pat. No. 5,151,423) (30.0 g; 123.2 mmol) was combined with NBS (48.2 g; 271.0 mmol) and benzoyl peroxide (0.42 g) in $CCl_4$ (210 ml). The reaction was heated to 80° C. for 10 hr. The mixture was cooled and let stand for 8 hr. The resulting precipitate was filtered, added to MeOH (200 ml) and the resulting mixture was stirred over 2 days. The solid was filtered and dried under vacuum to a constant weight.
Step B Preparation of Compounds (91a) and (91b)

The dibromo compound (90) from Step A (35.72 g; 88.97 mmol) above was dissolved in $CH_2Cl_2$ (1.5 L) and cooled to 0° C. Dropwise, DBU (15.96 ml) was added and the suspension stirred for 3 hr. The reaction mixture was concentrated redissolved in $CH_2Cl_2$ (1.5 L) filtered through a bed of silica gel and rinsed with 5% $EtOAc/CH_2Cl_2$ (4 L). The combined rinses were concentrated and purified by flash silica gel column chromatography into pure 5 and 6 monobromo substituted compounds eluting with 10–30% EtOAc/Hex, then 3% $EtOAc/CH_2Cl_2$.

Step C Preparation of Compound (92)

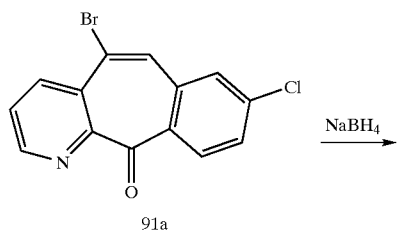

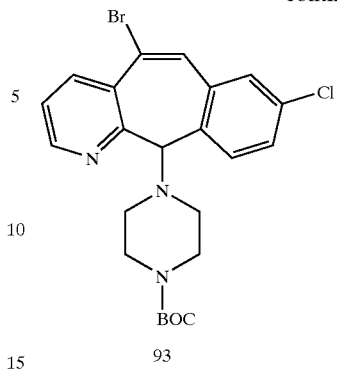

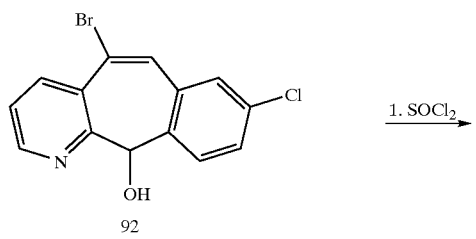

The 5-bromo substituted compound (91a) from Step B above (4.0 g; 12.45 mmol) was taken up in MeOH and cooled to 0° C. NaBH₄ (916.4 mg; 24.2 mmol) was added and the reaction mixture stirred for 5.5 hr. The solvent was removed and the resulting residue was used directly.

Step D Preparation of Compound (93)

The alcohol compound (92) from Step C above (3.98 g; 12 mmol) was dissolved in CH₂Cl₂ cooled to 0° C. and treated with 2,6-Lutidine (5.73 ml; 49 mmol). SOCl₂ (1.8 ml; 24.6 mmol) was added and the reaction was allowed to stir and come to room temperature over 3 hr. The reaction mixture was poured into 0.5N NaOH (80 ml) extracted and concentrated in vacuo. The crude product was taken up in CH₃CN and treated with 1,2,2,6,6-Pentamethylpiperidine (4.45 ml; 24.6 mmol) (Aldrich). The reaction was heated to 60–65° C. treated with tert-butyl 1-piperazinecarboxylate (2.32 g; 12 mmol) (Aldrich) and stirred over night under N₂ atmosphere. The reaction mixture was concentrated to dryness, redissolved in CH₂Cl₂ and washed with sat. aqueous NaCO₃. The organic layer was dried over Na₂SO₄, filtered and purified by flash silica gel column chromatography eluting with 1:4–1:2 EtOAc/Hexanes to afford the product as a white solid.

Preparative Example 25
Compound (94)

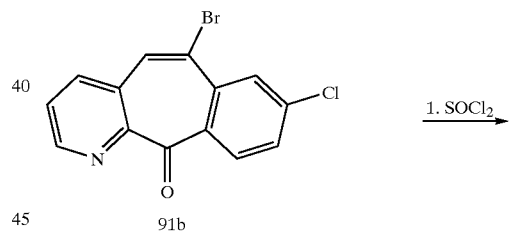

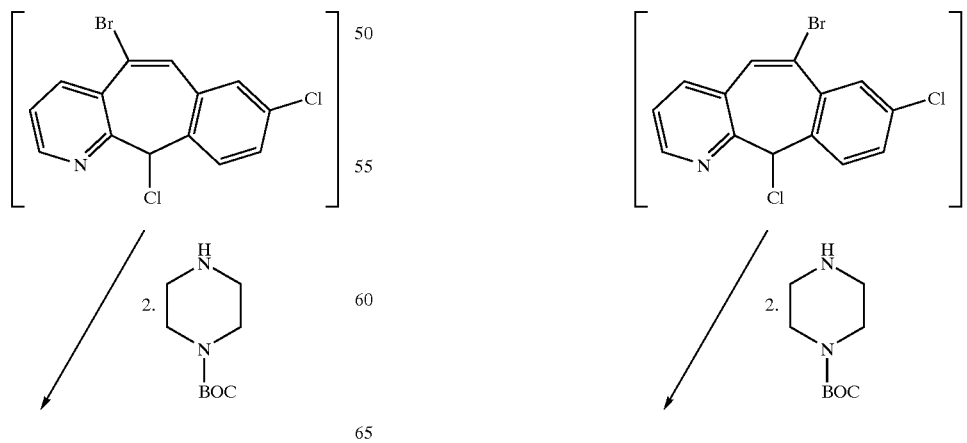

-continued

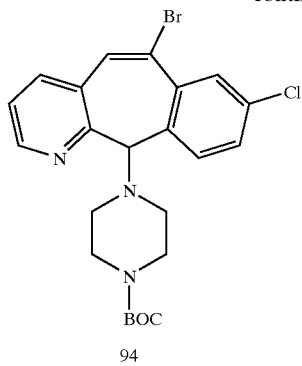
94

In essentially the same manner as in Preparative Example 24, Steps C-D, substituting the 6-Bromo substituted compound (91b) from Step B, for the 5-Bromo substituted compound (91a), Compound (94) was prepared (76.6 g, 100% yield).

Preparative Example 26

Step A Preparation of Compound (95)

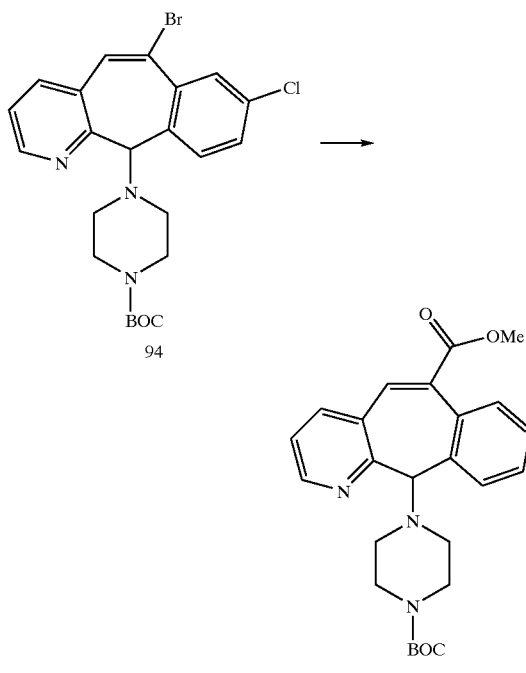

To a solution of Compound (94) from Preparative Example 25 (4.0 g, 8.16 mmol) in toluene (75 mL) and MEOH (20 mL), was added triphenyl phosphine (1.099 g, 4.08 mmol), DBU (1.7 g, 11.02 mmol) and palladium chloride (0.145 g, 0.82 mmol). The resulting solution was evacuated with CO at 100 psi and heated at 78° C.-82° C. for 5 hours, followed by the extraction with EtOAc-H₂O. The combined organic layer was then washed with brine, dried over Na₂SO₄, concentrated to dryness and purified by column chromatography, eluting with 30% EtOAc/70% Hexane to give Compound (95) (3.12 g, 100% yield, MH$^+$= 470.1).

B. Preparation of Compound (96)

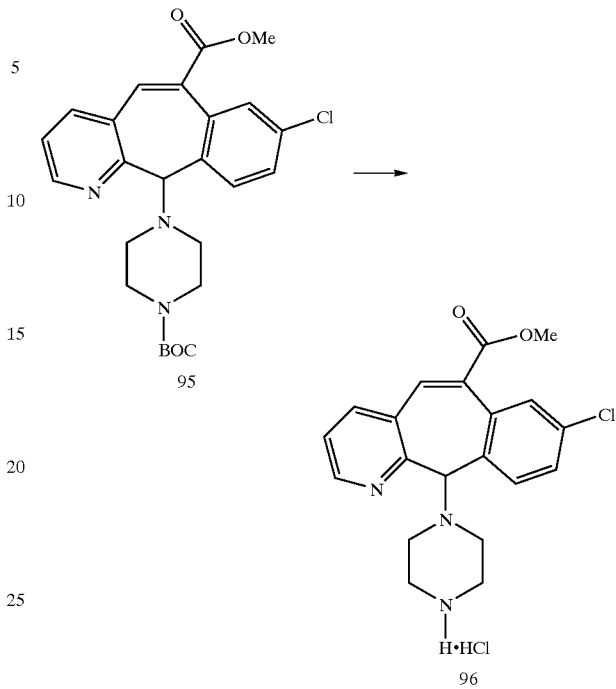

A solution of Compound (95) from Step A above (3.1 g, 6.6 mmol) in 4M HCl/Dioxane (120 mL) was stirred for 3 hours and then concentrated to dryness to give the crude salt of Compound (96) (3.89 g, 100% yield, MH$^+$=370.2)

Step C Preparation of Compound (97)

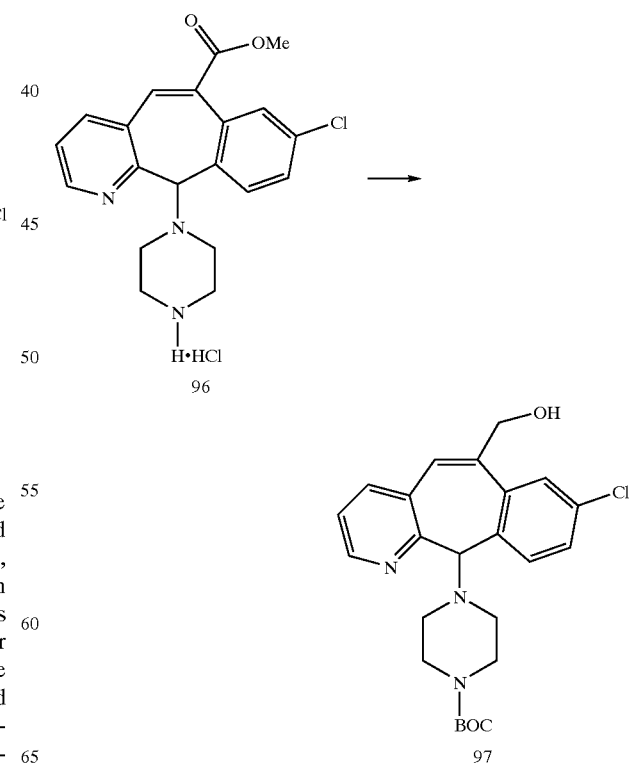

To a solution of Compound (96) from Step B above (3.43 g, 8.45 mmol) in THF (60 mL) at 0° C., was added DIBAL (7.21 g, 50.7 mmol). The resulting solution was warmed to room temperature, stirred overnight and then concentrated to dryness, followed by the addition of Boc anhydride (3.69 g, 16.9 mmol). The reaction was then extracted with $CH_2Cl_2$—$H_2O$, filtered over $Na_2SO_4$ and concentrated to dryness to afford Compound (97) (3.75 g, 100% yield, $MH^+$=442.4).

Step C.1 Alternate Preparation of Compound (97)

A solution of compound 95 from Step A above (23.46 g, 50.98 mmol) in $CH_2Cl_2$—MeOH—$H_2O$ (120 mL, 600 mL, 60 mL respectively) combined with LiOH (12.0 g, 350.88 mmol) was refluxed at 40° C. overnight. Solvent was removed from the reaction mixture. The residue was diluted with $CH_2Cl_2$, then acidified to pH 6 with 1N HCl. The organic layer was separated and washed with water, dried over $Na_2SO_4$ and concentrated. The product was dissolved in THF (285 mL) at 0° C. Triethyl amine (6 mL, 42.97 mmol) and ethyl chloroformate (4.1 mL, 42.97 mmol) were added and stirred at 0° C. for 1 h. The reaction mixture was filtered and the filtrate was cooled to −70° C. To this filtrate was added $NaBH_4$ (3.97 g, 104.94 mmol) and stirred for 1 h at −70° C. after which time 40 mL of MeOH was added dropwise. The solvents were removed and the residue taken up in methylene chloride, washed with sat. (aq) $NaHCO_3$, then brine, dried over $Na_2SO_4$ and concentrated to give Compound (97) as a solid.

Step D Preparation of Compound (98)

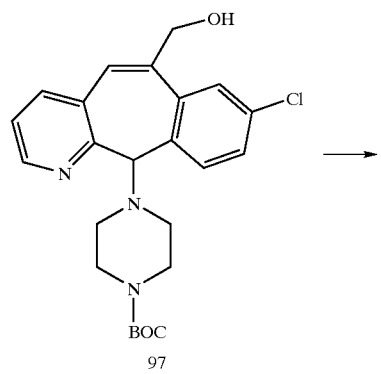

97

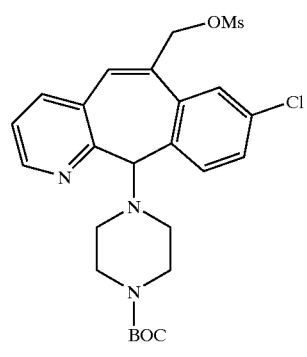

98

To a solution of Compound (97) from Step C above (3.74 g, 8.46 mmol) in $CH_2Cl_2$ (100 mL) was added triethyl amine (3.5 mL, 25.38 mmol) and methanesulfonyl chloride (1.45 g, 2.7 mmol). The resulting solution was stirred under nitrogen at room temperature for overnight and then washed with saturated $NaHCO_3$, then brine, and dried over $Na_2SO_4$ to give the mesylate compound (98) (3.86 g, 88% yield).

Step E Preparation of Compounds (99a) and (99b)

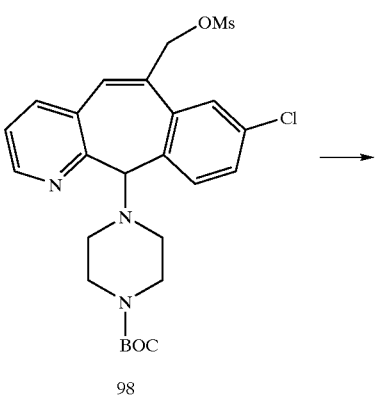

98

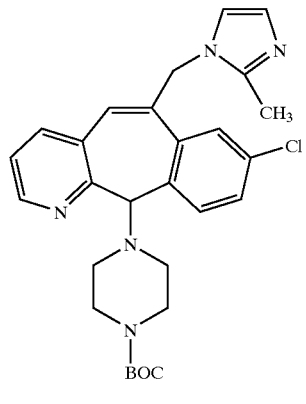

99a (isomer 1)
99b (isomer 2)

To a solution of 2-methylimidazole (2.43 g, 29.68 mmol) in DMF (30 mL) under $N_2$ was added NaH (0.53 g, 22.3 mmol) and stirred for 10 min, followed by the addition of Compound (98) from Step D above (3.86 g, 7.42 mmol). The solution was stirred over night. The solution was then concentrated to dryness and extracted with EtOAc-$NaHCO_3$, dried over $Na_2SO_4$, and concentrated. The crude product was purified by column chromatography, eluting with 2% MeOH—$NH_3$/98% $CH_2Cl_2$ to afford a mixture of isomers. Further separation was accomplished by Preparative HPLC Chiral AD Column chromatography, eluting with 25% IPA/75% hexane/0.2% DEA to give pure Compound (99a) (isomer 1) (0.160 g) and Compound (99b) (isomer 2) (0.140 g) ($MH^+$=506.1)

Step F Preparation of Compounds (100a) and (100b)

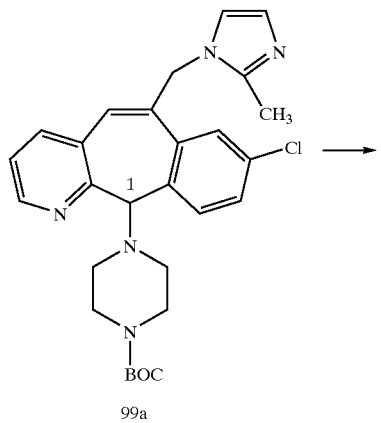

99a

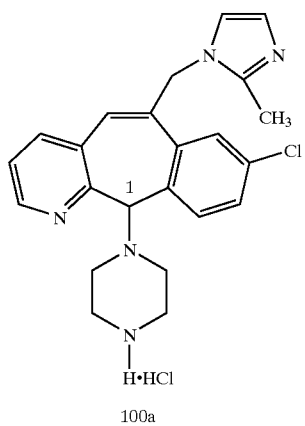

100a

A solution of Compound (99a) (isomer 1) from Step E above (0.105 g, 0.21 mmol) in 4M HCl/Dioxane (10 mL) was stirred at room temperature for 3 hours and concentrated to dryness to afford Compound (100a) (0.147 g, 100% yield)

Compound (99b) (isomer 2) from Step E was treated in the same manner as isomer 1 above, to afford Compound (100b) (isomer 2).

Examples 1 and 2

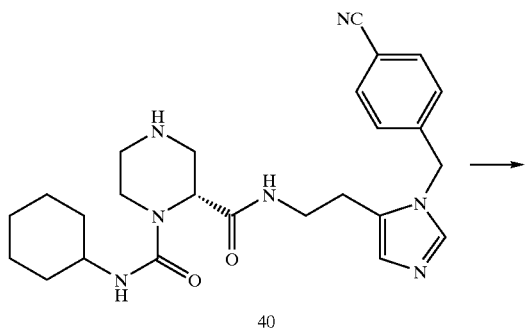

40

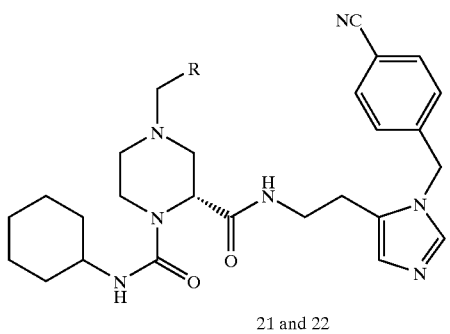

21 and 22

Sodium triacetoxyborohydride (75 mg, 0.336 mmol, 3.1 eq.) was added portion wise (3×25 mg) to a stirred solution of compound (40) (50 mg, 0.108 mmol, 1.0 eq.) from Preparative Example 11, Step B, and the appropriate aldehyde of the R group shown in the table below (0.336 mmol, 3.1 eq.), in a mixture of glacial acetic acid (0.5 ml) and anhydrous dichloromethane (10 ml) at 0° C. under a nitrogen atmosphere. The mixture was slowly (3 h) warmed to room temperature and stirred for another 12 h. The volatiles were removed under vacuum at 30° C. The residue was taken up in 1 N aqueous NaOH solution (10 ml) and extracted with dichloromethane (5×5 ml). The combined organic extracts were washed with brine (5 ml), dried over $Na_2SO_4$, filtered, and concentrated under vacuum at room temperature. The product was purified by preparative scale thin layer chromatography (using either $CH_2Cl_2$:2 N $NH_3$/MeOH=90:10 v/v or $CH_3CN$:2 N $NH_3$/MeOH=90:10 v/v as eluent) over silica gel to afford the compounds listed in the Table A below:

Reference: Abdel-Magid, A. F., Maryanoff, C. A., Carson, K. G. Tetrahedron Lett. 1990, 31, 5595.

TABLE A

| Example # | R | Compound # | Physical Data |
|---|---|---|---|
| 1 | naphthyl | 21 | MS: MH+ = 611.3 mp 100° C. (dec) 48% yield |
| 2 | pyridyl | 22 | MS: MH+ = 555.3 mp 80° C. (dec) 38% yield |

Example 3

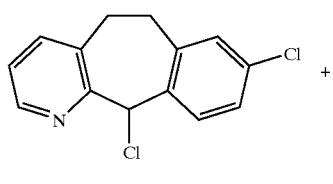
60

+

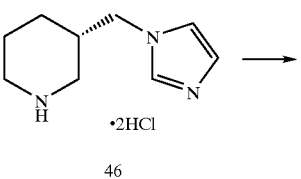
46

→

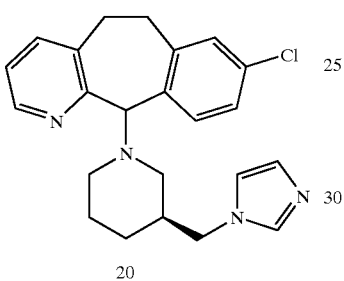
20

TEA (0.66 mL, 5.0 eq.) was added drop wise to a stirred solution of Compound (60) (0.25 g, 0.946 mmol) (see U.S. Pat. No. 5,151,423) and Compound (46) from Preparative Example 12, Step F (0.25 g, 1.1 eq.) in CH$_2$Cl$_2$ (5.0 mL). The resulting solution was stirred at room temperature for 24 h. then diluted with H$_2$O, neutralized with saturated NaHCO$_3$, and extracted with CH$_2$Cl$_2$. The combined organics were dried over Na$_2$SO$_4$, filtered, and concentrated under reduced pressure. The crude product was purified by flash chromatography using a 5% (10% NH$_4$OH in MeOH) in CH$_2$Cl$_2$ solution as eluent to yield Compound (20) as the first eluting isomer and a mixture of diastereomers:

Compound (20):LCMS: MH$^+$=393; mp=71–75° C.; [α]$_D^{20}$=−65° (3.97 mg in 5.0 mL MeOH).

Example 4

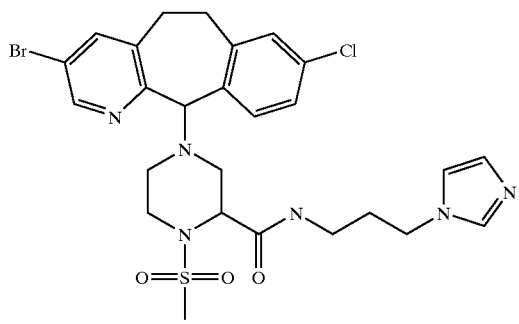
23

Compound (49) from Preparative Example 15, Step A, was reacted with Compound (52) from Preparative Example 17 using essentially the same procedure as in Example 3, to obtain Compound (23); FABMS (M+1)=623.

Example 5

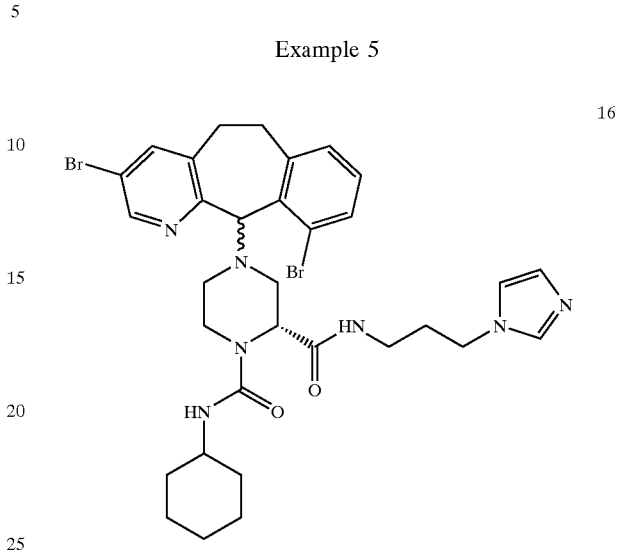
16

Compound (34) (0.9 gm) from Preparative Example 5 was reacted with compound (59) from Preparative Example 20, Step D 0.36 gm, 1 mmol) using essentially the same procedure as in Example 3, to obtain Compound (16); FABMS (M+1)=715.

Example 6

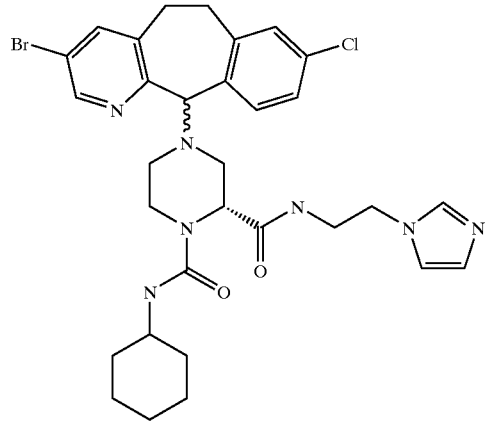
17

Compound (53) from Preparative Example 18 was reacted with Compound (49) from Preparative Example 15, Step A, using essentially the same procedure as in Example 3, to obtain Compound (17); FABMS (M+1)=656.

Example 7

Compound 18

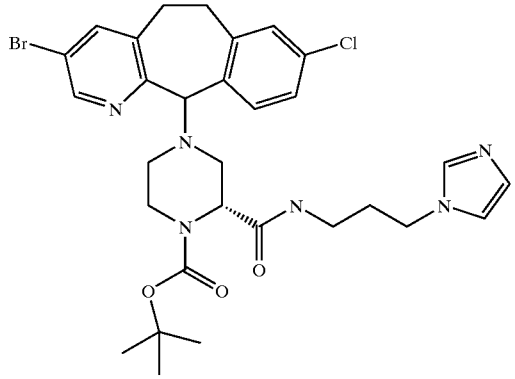

Compound (54)(0.9 gm) from Preparative Example 19 was reacted with Compound (49) from Preparative Example 15, Step A, using essentially the same procedure as in Example 3, to obtain Compound (18).

Example 8

Compound 19

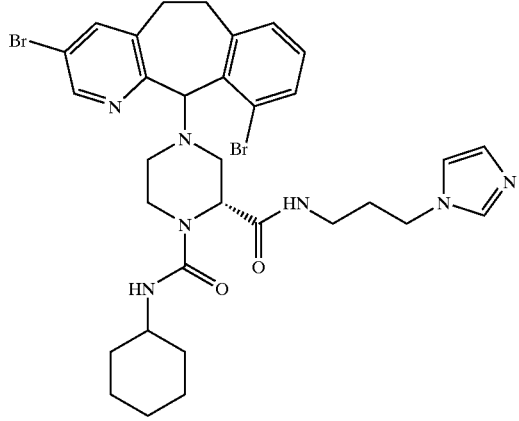

Compound (16) from Example 5 was further purified by HPLC on a Chiralcel AD column eluting with 30% Isopropanol/Hexanes: 0.2% DEA, to afford the pure isomer A Compound (19).

Example 9
Compounds 13 and 13a

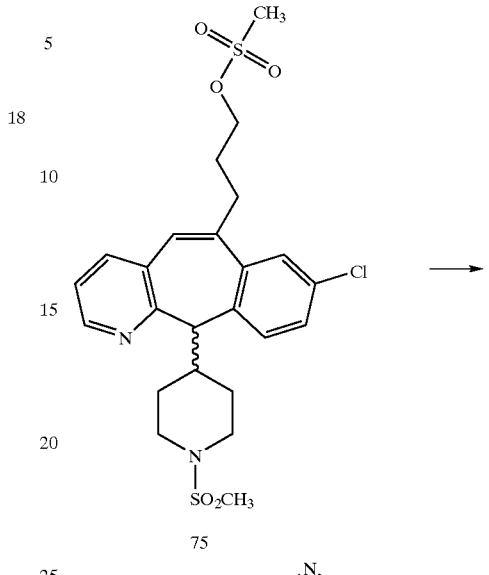

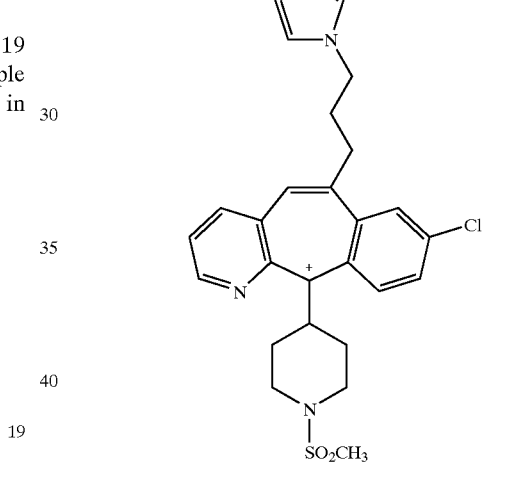

To a solution of compound (75) from Preparative example 22, Step D (0.2 g, 0.41 mmole) in DMF (7 ml) was added imidazolylsodium (0.054 g, 0.61 mmol). The reaction mixture was heated to 90° C. for 2 h then cooled and the DMF was removed. To the residue was added saturated sodium bicarbonate and the solution was extracted with $CH_2Cl_2$. The organic layer was dried over magnesium sulfate, filtered and concentrated to dryness. The crude product was purified by Biotage column chromatography eluting with 5% $CH_3OH$: (saturated with ammonia)-$CH_2Cl_2$, to afford the title compound as an enantiomeric mixture. The mixture was separated into pure enantiomers on Prep HPLC Chiral AD column eluting with 35–40% Isopropanol-Hexane: 0.2% Diethyl amine, to give the title compounds (13) and (13a) MS 497 (MH$^+$).

Example 10

Compounds 14 and 14a

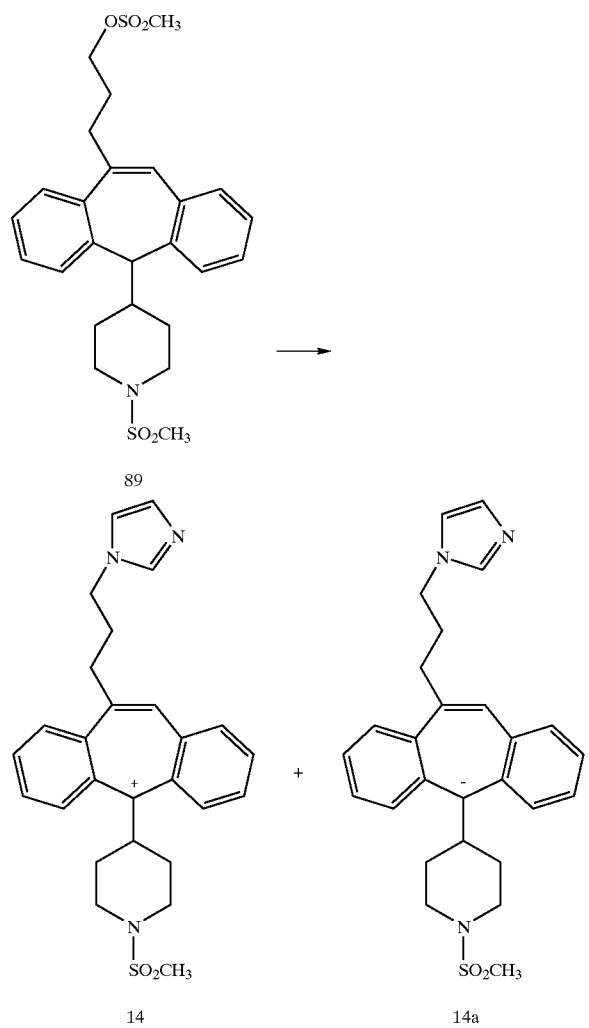

In a similar manner as described in Example 9 above, imidazolylsodium was added to a solution of the compound (89) from Preparative example 23, Step L, in DMF (7 ml). The reaction mixture was heated to 90° C. for 2 h then cooled and the DMF was removed. To the residue was added saturated sodium bicarbonate and the solution was extracted with $CH_2Cl_2$. The organic layer was dried over magnesium sulfate, filtered and concentrated to dryness. The crude product was purified by Biotage column chromatography eluting with 5% $CH_3OH$: (saturated with ammonia)-$CH_2Cl_2$, to afford the title compound as an enantiomeric mixture. The mixture was separated into pure enantiomers on Prep HPLC Chiral AD column eluting with 35–40% Isopropanol-Hexane: 0.2% Diethyl amine, to give the title compounds (14) and (14a) MS 497 (MH$^+$).

Example 11

Compound 24

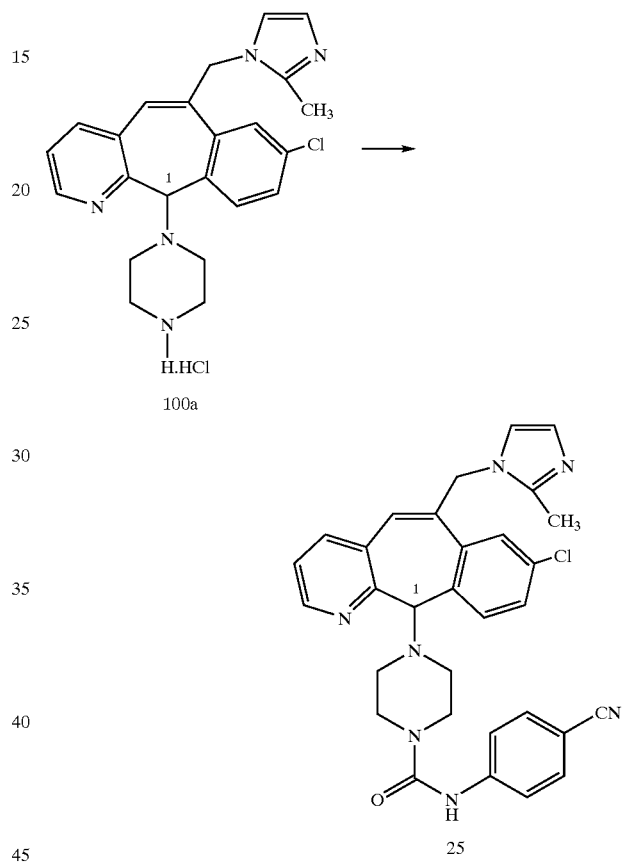

To a solution of compound 100a (1.3 g, 2.94 mmol) in $CH_2Cl_2$ (60 mL) was added triethyl amine (1.3 mL, 9.4 mmol) and p-cyano phenyl isocyanate (0.466 g, 3.24 mmol). The resulting solution was stirred at room temperature overnight, followed by the extraction with $CH_2Cl_2$ and saturated $NaHCO_3$. The organic layer was dried over $Na_2SO_4$, evaporated and the residue purified by column chromatography, eluting with 1% -2% MeOH—$NH_3$/98% $CH_2Cl_2$ to afford compound (24) (0.870 g, 48% yield) isomer 1; MS MH+=550.

In Vitro *Plasmodium falciparum* Growth Inhibition Assay

The growth activity of *P. falciparum* was determined by measuring the uptake of the radiolabeled nucleic acid precursor [3H]-hypoxanthine from the media into infected erythrocytes by a method similar to that reported by Jomaa et al (1999). In this method human red blood cells (RBC) were infected with *P. falciparum* (strain C10, partially chloroquine resistant strain) to 0.4% parasitemia (0.4% of the RBC contain at least 1 parasite). The infected human RBC cells were adjusted to a hematocrit of 2% and 200 µl was plated into 96 well plates. DMSO solutions of inhibitors were added to the plates to make final concentrations of inhibitors from 20 µM to 0.2 µM and a final concentration of DMSO between 0.2 and 1%. The inhibitor-RBC solutions were incubated for 48 hours followed by the addition of [3H]-hypoxanthine to each well and further incubated for 24 hours. The incorporation of [3H]-hypoxanthine into the parasite DNA was measured by acid precipitating the nucleic acid content onto filters, washing the filters and counting the incorporated radioactivity in a scintillation counter. Controls were run to demonstrate that DMSO at levels<0.5% did not inhibit parasite growth while a 1% DMSO solution inhibited growth 30%. The $ED_{50}$ for fosmidomycin and chloroquine, known inhibitors of *P. falciparum*, were 0.6 and 0.26 µM, respectively.

Compounds of the present invention exhibit a *P. falciparum* $ED_{50}$ range of between 0.05 µM and 8.6 µM.

Reference

Jomaa et al, 1999, Science 285, 1573–1576. "Inhibitors of the Nonmevalonate Pathway of Isoprenoid biosynthesis as Antimalarial Drugs".

Administration and Dosage

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. Examples of liquid forms are water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations, which are intended to be converted, shortly before use, to liquid form preparations for either oral or parenteral administration. Such liquid forms include solutions, suspensions and emulsions.

The compounds of the invention may be deliverable transdermally. The transdermal compositions can take the form of creams, lotions, aerosols and/or emulsions and can be included in a transdermal patch of the matrix or reservoir type as are conventional in the art for this purpose.

Preferably, the compounds of the invention are administered orally. Pharmaceutical compositions can contain any one of the compounds1–23 used in the methods of the invention in combination with one or more additional compounds, which are useful in preventing or treating malaria. Additional compounds include but are not limited to the use of quinolines (i.e., Chloroquine), folic acid antagonists (e.g. pyrimethamine), sulfonamides (e.g. sulfadiazine), antibiotics (e.g. tetracycline) and compounds which reverse Chloroquine resistance i.e. inhibitors of multidrug resistance (e.g. tetrandrine).

Preferably, the pharmaceutical preparation is in a unit dosage form. In such form, the preparation is subdivided into unit doses containing therapeutically effective amounts of the active component, i.e., amounts that inhibit malaria.

The compounds of this invention are administered to a patient in need of such treatment (e.g. a mammal, such as a human being) in an effective amount, e.g. a therapeutically effective amount, or a malaria inhibitory effective amount. An effective amount is that amount necessary to inhibit FPT, and thereby inhibit the malarial parasite.

The quantity of active compound in a unit dose of preparation may be varied or adjusted from about 1.0 mg to about 4500 mg, preferably from about 10.0 mg to about 1000 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day i.e., the total daily dosage may be divided and administered in portions up to two to four times over a 24 hour period.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 10 mg/day to about 9000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for treating malaria comprising administering to a human in need of such treatment an effective amount of a compound selected from:

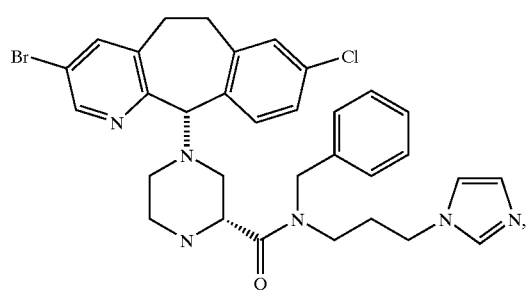

2
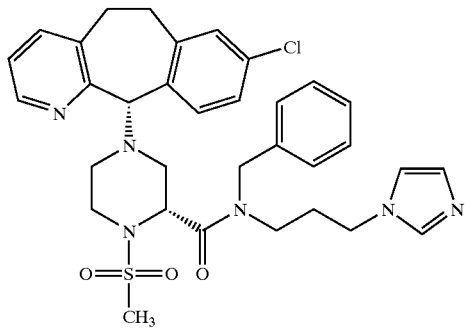
3
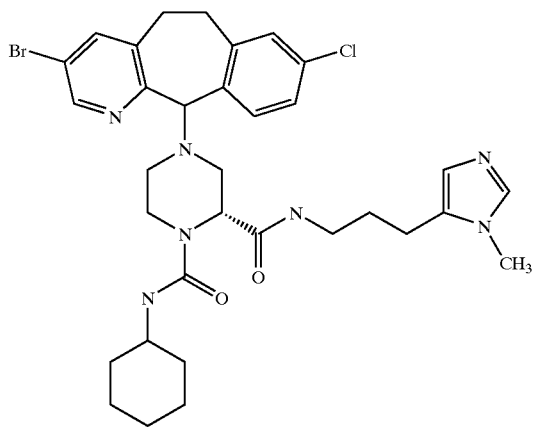
4
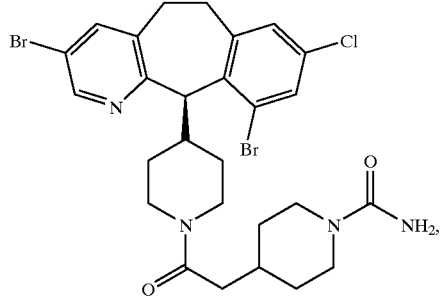
5
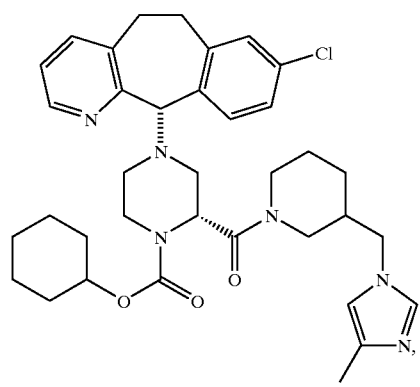
6
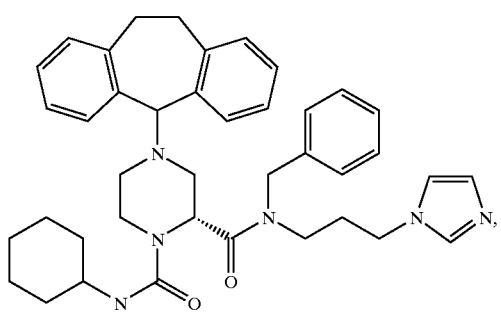
7
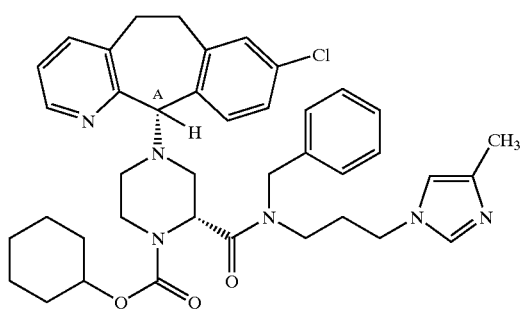
8
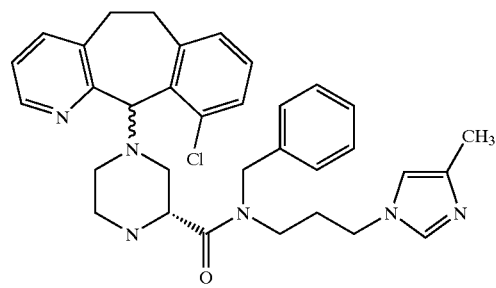
9
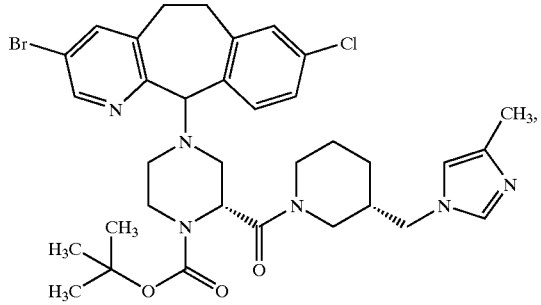

10
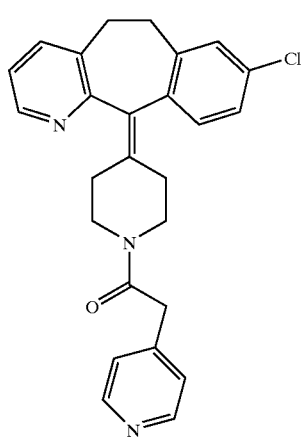
11
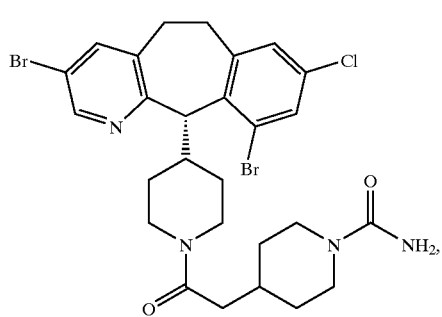
12
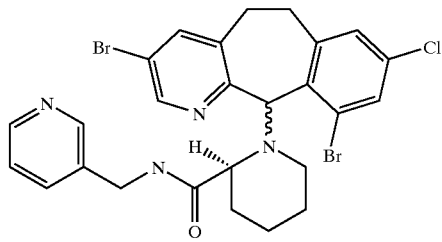
13
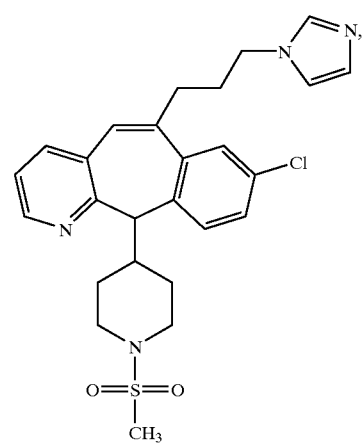
14
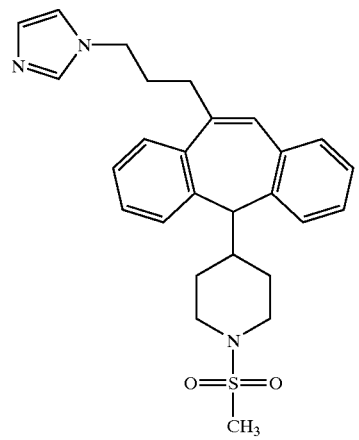
15
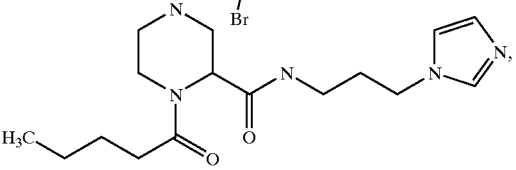
16
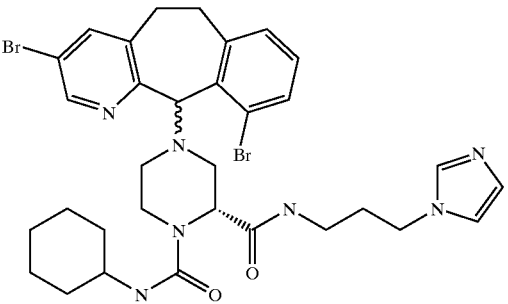
17

18
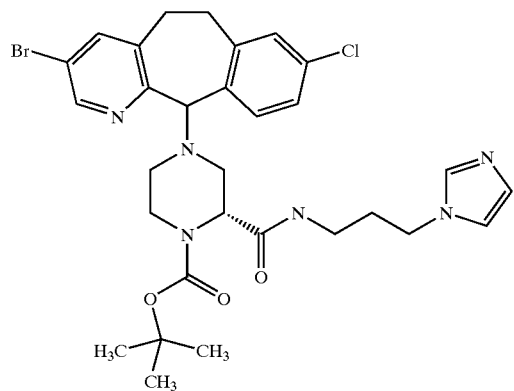
19
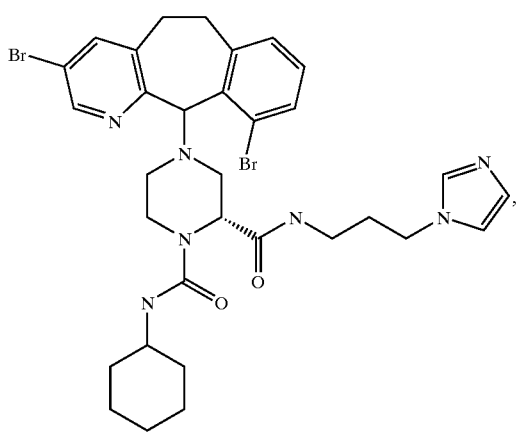
20
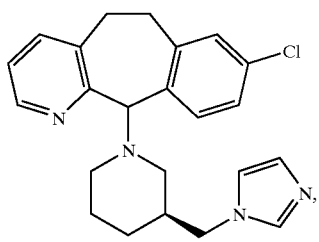
21
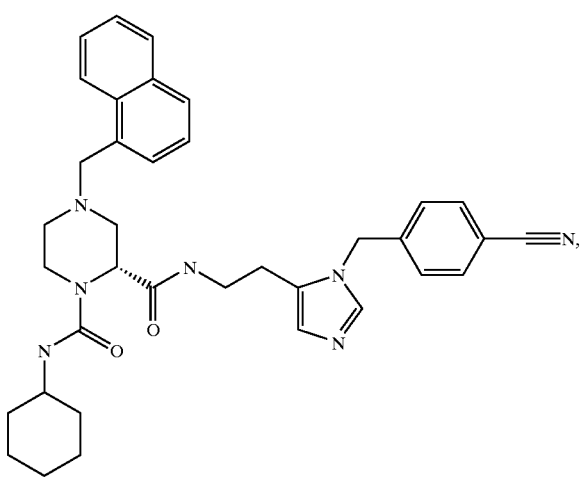
22
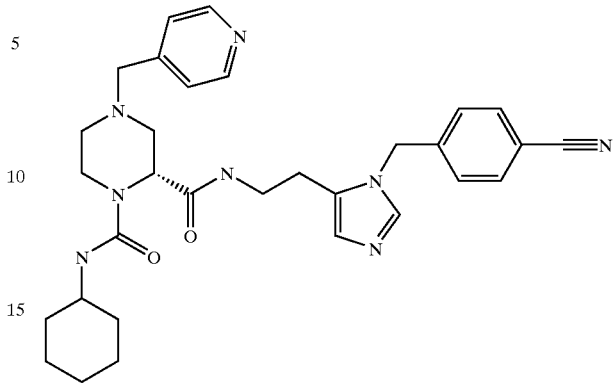
23
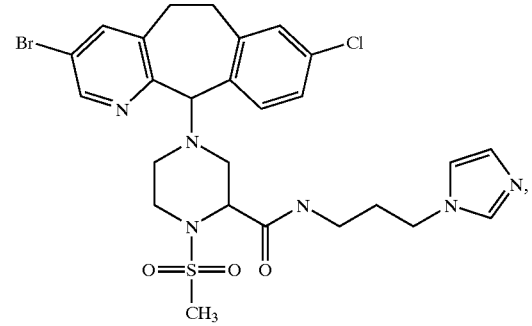
24
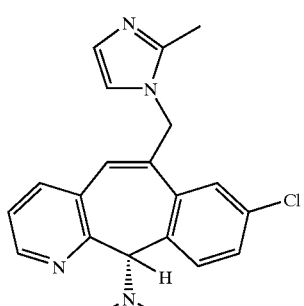
25
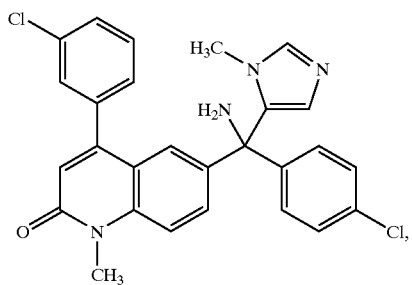

2. The method of claim 1 wherein the compound is:

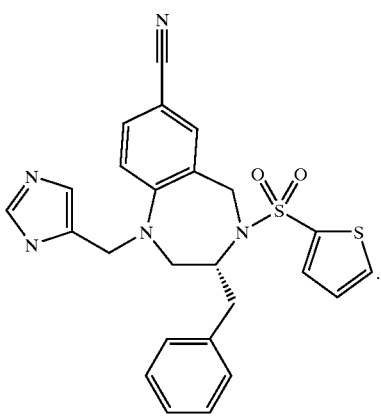

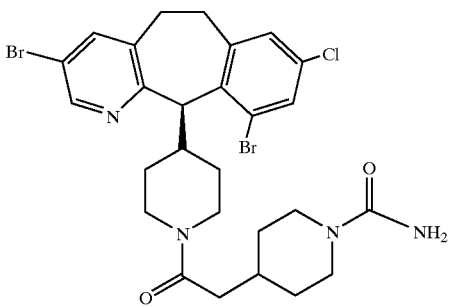

3. A method for treating malaria comprising administering to a patient in need of such treatment an effective amount of a compound used in the method of claim 1, in combination with an effective amount of an additional antimalarial agent and/or an additional agent for reversing antimalarial resistance.

4. A method for treating malaria comprising administering to a patient in need of such treatment an effective amount of the compound used in the method of claim 2, in combination with an effective amount of an additional antimalarial agent and/or an additional agent for reversing antimalarial resistance.

5. The method of claim 3, wherein said compound is administered prior to, concurrent to or subsequent to the administration of said additional antimalarial agent and/or said agent for reversing antimalarial resistance.

6. The method of claim 3 wherein said additional antimalarial agent is selected from the group comprising:

a) quinolines,
b) folic acid antagonists,
c) sulfonamides, and
d) antibiotics.

7. The method of claim 3 wherein said agent for reversing antimalarial resistance is an inhibitor of multidrug resistance.

8. The method of claim 4, wherein said compound is administered prior to, concurrent to or subsequent to the administration of said additional antimalarial agent and/or said agent for reversing antimalarial resistance.

9. The method of claim 4 wherein said additional antimalarial agent is selected from the group comprising:

a) quinolines,
b) folic acid antagonists,
c) sulfonamides, and
d) antibiotics.

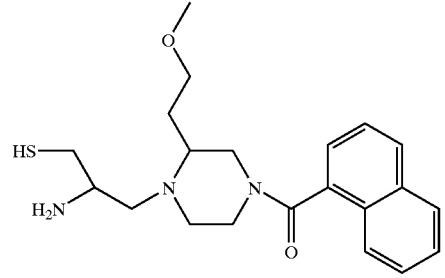

* * * * *